US006459017B1

(12) United States Patent
Jeknic et al.

(10) Patent No.: US 6,459,017 B1
(45) Date of Patent: Oct. 1, 2002

(54) IRIS TRANSFORMATION METHOD

(75) Inventors: Zoran Jeknic, Corvallis, OR (US);
Richard C. Ernst, Silverton, OR (US);
Tony H. H. Chen, Philomath, OR (US)

(73) Assignees: The State of Oregon Acting By and Through the State Board of Higher Education on Behalf of Oregon State University, Corvallis, OR (US);
Cooley's Gardens, Inc., Silverton, OR (US)

( * ) Notice: Subject to any disclaimer, the term of this patent is extended or adjusted under 35 U.S.C. 154(b) by 0 days.

(21) Appl. No.: 09/607,102

(22) Filed: Jun. 29, 2000

(51) Int. Cl.$^7$ .............................. A01H 4/00; A01H 5/02; A01H 5/00; C12N 15/82; C12N 15/84; C12N 5/04

(52) U.S. Cl. ...................... 800/278; 435/468; 435/469; 435/470; 435/430; 435/419; 800/323; 800/279; 800/293; 800/294; 800/282; 800/300

(58) Field of Search ................................ 435/419, 430, 435/468, 469, 470; 800/278, 279, 282, 323, 294, 293, 300

(56) References Cited

U.S. PATENT DOCUMENTS

| 5,340,730 A | 8/1994 | Graves et al. .............. 800/294 |
| 5,349,125 A | 9/1994 | Holton et al. ............... 800/286 |
| 5,410,096 A | 4/1995 | Meyer et al. ............ 800/323.1 |
| 5,569,832 A | 10/1996 | Holton et al. .............. 800/298 |
| 5,589,613 A | 12/1996 | Firoozabady et al. ....... 800/294 |
| 5,679,558 A | 10/1997 | Göbel et al. ................ 800/292 |
| 5,712,135 A | 1/1998 | D'Halluin et al. .......... 800/292 |
| 5,861,487 A | 1/1999 | Holton et al. .............. 530/370 |
| 5,874,265 A | 2/1999 | Adams et al. .............. 800/260 |
| 5,880,332 A | 3/1999 | Camara et al. ............. 800/282 |
| 5,948,955 A | 9/1999 | Holton et al. .............. 800/298 |
| 6,037,522 A | 3/2000 | Dong et al. ................. 800/278 |

OTHER PUBLICATIONS

Jeknic et al. 1999, Genetic transformation of *Iris germanica* mediated by *Agrobacterium tumefaciens*. The Journal of the Americal Society of Horitcultural Science 124(6):575–580.*
Shimizu et al. 1997, Plant regeneration from suspension culture of *Iris germanica*. Plant Cell, Tissue and Organ Culture 50:27–31.*
Smith et al. 1995, *Agrobacterium tumefaciens* transformation of monocotyledons. Crop Science 35(2):301–309.*
Hanson et al. 1999, Recent advances in the transformation of plants. Trends in Plant Science 4(6):226–230.*
Halperin, Alternative Morphogenetic Events in Cell Suspensions, *Amer. J. Bot.*, 53:443–453, 1966.
Fujino et al., Multiplication of Dutch Iris (*Iris hollandica*) by Organ Culture, *J. Jpn. Soc. Hort. Sci.*, 41:66–71, 1972.
Meyer, Jr., et al., Propogation of Tall Bearded Irises by Tissue Culture, *HortScience*, 10:479–480, 1975.

Hussey, *Scientia Hort.*, Propagation of Dutch Iris by Tissue Culture, 4:163–165, 1976.
Radoojević et al., Somatic Embryogenesis in Tissue Culture of Iris (*Iris pumila* L.), *Acta Hort.*, 212:719–723, 1987.
van der Linde et al., In Vitro Propogation of *Iris Hollandica*, *Acta Hort.* 226:121–128, 1988.
Kamo et al., The Establishment of Cell Suspension Cultures of Gladiolus that Regenerate Plants, *In Vitro Cell Dev. Biol.*, 26:425–430, 1990.
Laublin et al., In vitro plant regeneration via somatic embryogenesis from root culture of some rhizomatous irises, *Plant Cell Tiss. Org. Cult.*, 27:15–21, 1991.
Yabuya et al., In Vitro propagation of Japanese garden iris, *Iris ensata* Thunb., *Euphytica* 57:77–81, 1991.
Conner and Dommisse, Monocotyledonous Plants as Hosts for Agrobacterium, *Intl. J. Plant. Sci.* 153:550–555, 1992.
Radojević and Subotić, Plant Regeneration of *Iris setosa* Pall. Through Somatic Embryogenesis and Organogenesis, *J. Plant Physiol.*, 139:690–696, 1992.
Kuehnle and Sugii, Transformation of Dendrobium orchid using particle bombardment of protocorms, *Plant Cell Rpt.*, 11:484–488, 1992.
Gozu et al., In Vitro propagation of *Iris pallida*, *Plant Cell Rpt.*, 13:12–16, 1993.
Jéhan et al., Plant regeneration of *Iris pallida* Lam. And *Iris germanica* L. via somatic embryogenesis from leaves, apices and young flowers, *Plant Cell Rep.*, 13:671–675, 1994.*
Kamo et al., Stable Transformation of Gladiolus Using Suspension Cells and Callus, *J. Amer. Soc. Hort. Sci.*, 120:347–352, 1995.*
Smith and Hood, *Agrobacterium tumefaciens* Transformation of Monocotyledons, *Crop Sci.*, 35:301–309, 1995.*
Vain et al., Foreign Gene Delivery into Monocotyledonous Species, *Biotechnol. Adv.*, 13:653–671, 1995.*
Anzai et al., Transformation of Phalaenopsis by Particle Bombardment, *Plant Tis. Cult. Let.*, 13:265–272, 1996.*
Chen and Kuehnle, Obtaining Transgenic Anthurium through Agrobacterium–mediated Transformation of Etiolated Internodes, *J. Amer. Soc. Hort. Sci.*, 121:47–51, 1996.*
Shimizu et al., Plant regeneration from protoplasts of *Iris germanica* L., *Euphytica*, 89:223–227, 1996.*

(List continued on next page.)

Primary Examiner—David T. Fox
Assistant Examiner—David H Kruse
(74) Attorney, Agent, or Firm—Klarquist Sparkman, LLP

(57) ABSTRACT

Methods of transformation and regeneration of *Iris germanica* cell suspensions are disclosed. Also disclosed are transgenic *Iris germanica* cells and plants made by the disclosed methods.

20 Claims, 9 Drawing Sheets

OTHER PUBLICATIONS

Shimizu et al., Plant regeneration from suspension culture of *Iris germanica*, *Plant Cell Tiss. Org. Cult.* 50:27–31, 1997.*

Tingay et al., *Agrobacterium tumefaciens*–mediated barley transformation, *Plant J.*, 11:1369–1375, 1997.*

Komari et al., Advances in cereal gene transfer, *Plant Biotechnol.*, 1:161–165, 1998.

Jeknic et al., Genetic Transformation of *Iris germanica* Mediated by *Agrobacterium tumefaciens*, *J. Amer. Soc. Hort. Sci.*, 124:575–580, 1999.

Wang et al., Efficient Plant Regeneration from Suspension–cultured Cells of Tall Bearded Iris, *HortScience*, 34:730–735, 1999.

Wang et al., Improved Plant Regeneration from Suspension–cultured Cells of *Iris germanica* L. 'Skating Party', *HortScience*, 34:1271–1276, 1999.

Wenck et al., High–efficiency Agrobacterium–mediated transformation of Norway spruce (*Picea abies*) and loblolly pine (*Pinus taeda*), *Plant Mol. Biol.*, 39:407–416, 1999.

Yang et al., Genetic transformation of Cymbidium orchid by particle bombardment, *Plant Cell Rpt.*, 18:978–984, 1999.

Belarmino and Mii, Agrobacterium–mediated genetic transformation of a phalaenopsis orchid, *Plant Cell Rept.*, 19:435–442, 2000.

* cited by examiner

IRIS TRANSFORMATION METHOD

BACKGROUND

Iris is a winter hardy, herbaceous perennial consisting of approximately 300 species, many of which are popular ornamentals in the temperate regions of the Northern Hemisphere. Most horticulturally important irises are bearded species and their hybrids are derived from species native to the Near East and Europe (Kohlein, Iris, Timber Press, Portland, Oreg., 1987). In addition to their ornamental value, certain species, such as *Iris pallida* Lam. and *Iris germanica* L., contain an essential oil composed partly of irones that can be extracted from rhizomes (Jéhan et al., *Plant Cell Rpt.*, 13:671–675, 1994; Kohlein, Iris, Timber Press, Portland, Oreg., 1987). The irones (violet-scented ketonic compounds) are expensive materials commonly used in cosmetics and perfumes (Gozu et al., *Plant Cell Rpt.*, 13:12–16, 1993).

*Iris germanica* is one of the horticulturally most important tall bearded irises in the genus. Hundreds of valuable cultivars from this species have been developed and cultivated commercially as perennial ornamental plants. Traditionally, rhizomatous iris plants are propagated by splitting rhizomes, with a maximum annual yield of 10 plants/rhizome (Jéhan et al., *Plant Cell Rep.*, 13:671–675, 1994). This practice is inefficient and slow, especially for propagating new cultivars for commercial use. Propagation by seed is impractical because of low germination rates and the allogamous nature of iris. Therefore, a more efficient propagation method is needed.

Plant regeneration from somatic tissues is generally considered a prerequisite to genetic transformation. Many efforts have been made to induce plant regeneration via in vitro callus culture of various explant types from several iris species (Fujino et al., *J. Jpn. Soc. Hort. Sci.*, 41:66–71, 1972; Gozu et al., *Plant Cell Rep.*, 13:12–16, 1993; Hussey, *Scientia Hort.*, 4:163–165, 1976; Laublin et al., *Plant Cell Tiss. Org. Cult.*, 27:15–21, 1991; Meyer, Jr., et al., *HortScience*, 10:479–480, 1975; Radojević and Landre, *Proc. 7th Intern Congr. Plant Tissue and Cell Culture*, Amsterdam, The Netherlands, (Abstr.) B4-100, 1990; Radojević, et al. *Acta Hort.*, 212:719–723, 1987; Radojević and Subotić, *J. Plant Physiol.*, 139:690–696, 1992; van der Linde et al., *Acta Hort.* 226:121–128, 1988; Yabuya et al., *Euphytica* 57:77–81, 1991). In *I. germanica*, Reuther (*Ber. Deutsch Bot. Ges.*, 90: 417–437, 1977) induced embryogenic calli from zygotic embryos and Jéhan et al. (*Plant Cell Rep.*, 13:671–675, 1994) regenerated plants via somatic embryogenesis from leaves, rhizome apices, and immature flowers. Shimizu et al. cultured protoplasts and regenerated plants via somatic embryogenesis (*Euphytica*, 89:223–227, 1996). The same group induced embryogenic calli from three cultivars of *I. germanica*, but was able to induce regeneration from suspension cultures in only one (Shimizu et al., *Plant Cell Tiss. Org Cult.*, 50:27–31, 1997). The low efficiency of plant regeneration in *I. germanica* and other iris species has hindered development of a suitable system for genetic transformation. Genetic transformation of iris has not previously been reported.

Strong consumer demand means increased challenges in developing new iris cultivars with novel characteristics. Unfortunately, most efforts in iris breeding have been primarily intraspecific because of the high degree of incompatibility between species. Thus, the search for an alternative breeding method is imperative. Genetic transformation and regeneration offers an alternative approach for introducing desirable traits, such as resistance to herbicides, diseases, and insects; or developing desired floral characteristics such as novel colors.

SUMMARY

The inventors have developed efficient *A. tumefaciens*-mediated and microparticle bombardment transformation methods and regeneration methods for ornamental monocots such as Iris. With the provision herein of such transformation and regeneration methods, rapid and efficient iris transformation and/or in vitro propagation is now enabled.

Embodiments of the invention may include methods of transforming iris cells; such methods involve introducing a recombinant nucleic acid molecule into an iris cell, initiating callus formation from the iris cells; and selecting transformed cells. Selection of transformed cells can, for instance, involve growing the cells on medium that provides a selective pressure towards the transformed cells. The recombinant nucleic acid can be introduced in any manner, including co-cultivating the iris cells with Agrobacterium (e.g., *A. tumefaciens* or rhizogenes); bombarding the cells with nucleic acid-coated microprojectiles; and electroporating or PEG treatment of protoplasts of the cells.

In certain embodiments of the invention, the iris cells to which the recombinant nucleic acid is introduced are in suspension culture; however, they could also be in callus culture. Alternatively, these cells could be cells excised directly from an iris plant, such as meristematic cells or other partially differentiated or de-differentiated cells. Cells useful for transformation and/or regeneration as described herein include cells from iris shoot tissue, root tissue, rhizome tissue, and flower or other reproductive tissue.

Specific methods disclosed further include regenerating transformed shoots from the transformed plant cells. The disclosed methods may also include inducing root formation in the transformed cells and/or shoots.

Another embodiment of the invention includes a method for transforming iris cells, wherein the iris cells are co-cultivated with an Agrobacterium that contains a recombinant vector (e.g., a regular binary vector, a co-integrating vector, or a super binary vector). Such a recombinant vector can include a transfer DNA region, and may further include at least one (but often, more than one) protein-encoding sequence. Such protein-encoding sequences can include, for instance, selectable marker genes and/or desired trait genes (e.g., those encoding irone synthetic proteins, plant pigment synthetic proteins, pesticide resistance proteins, herbicide resistance proteins, or disease resistance proteins).

Methods of transformation and regeneration as disclosed herein find equal application in any species of the genus Iris, including *Iris germanica, I. hollandica, I. pallida, I. setosa, I. lavigata*, and *I. pumila*. Likewise, the described methods are effective independent of the ploidy of the *Iris*, and therefore find equal application in, for instance, diploid, tetraploid, and hexaploid varieties, as well as variants that are aneuploid for one or more chromosomes.

Also encompassed by this invention are cells produced by the disclosed transformation and/or regeneration methods, and plants, plant parts (including seeds and flowers), and plant progeny produced using such transformed and/or regenerated cells. In certain embodiments, these cells/tissues/plants will express one or more traits that the cell source material (source explant or explant) did not posses, such as an altered flower color, flowering time, disease resistance, herbicide resistance, pesticide resistance, or senescence schedule.

A further embodiment of the invention includes a method for culturing iris cells and regenerating iris plants, which includes growing suspension culture in MS-L medium supplemented with an auxin and a cytokinin (e.g., about 5 $\mu$M 2,4-D and about 0.5 $\mu$M Kin) in the dark for a period of time (for instance, six weeks) at 25° C., and isolating relatively small cell clusters (e.g., those about $\leq$520 $\mu$m) from the suspension culture. This method can further include inoculating the isolated clusters into an appropriate shoot induction medium (e.g., MS-I medium supplemented with about 2.5 to about 12.5 $\mu$M Kin and 0.0 to about 0.5 $\mu$M NAA) and growing the clusters in the dark for another period of time (for instance, about six weeks) at 25° C. to initiate differentiation. Differentiated clumps can then be isolated, and placed on shoot elongation and development medium (e.g., MS-D with 1.25 $\mu$M DA) under light (for instance, about 50 $\mu$m/m$^2$s) at 23° C. for a period sufficient to regenerate shoots and/or plantlets (which in some embodiments will be about six weeks). Regenerated shoots and/or plantlets can be transferred to root initiation medium, and subsequently transplanting rooted shoots and/or plantlets to soil in a greenhouse.

In a further embodiment of the invention, iris cells can be transformed with a recombinant nucleic acid molecule prior to being regenerated by this method. Such regeneration can for instance include co-cultivation with A. tumefaciens or microparticle bombardment.

The foregoing and other features and advantages of the invention will become more apparent from the following detailed description of several embodiments, which proceeds with reference to the accompanying figures and tables.

(A) Assay for expression of the GUS gene immediately after three days co-cultivation. Many iris cells and small aggregates were stained dark blue (which shows as black in the figure). (B) A cell clump that proliferated on the first selection medium ten days after co-cultivation with A. tumefaciens is shown. (C) The majority of clumps that proliferated on the first selection media tested GUS-positive. Most of clumps (as shown here) were stained dark blue, indicating very strong expression of the GUS gene.

(D) Independent callus lines obtained through two-step selection were assayed for expression of the GUS gene activity before being transferred to shoot induction media (MS-I). (E) Hygromycin-resistant, GUS-positive callus line; numerous shoot primordia were present after three weeks on the MS-I medium. (F) A number of the shoot primordia were excised and stained for the expression of the GUS gene. Most of them tested GUS-positive (as shown).

(G) Plantlets with well-developed shoots and roots, shown here after 4 weeks on the MS-R medium. (H) Transgenic plants in the greenhouse one week after acclimatization on the mist bench. (I) Leaves from putative transgenic plants were assayed for the functional expression of NPTII gene (using the leaf-bleach assay). Bleaching was substantially reduced in the successful transformants. Key: 0, 50, 100, and 200 refer to 0, 50, 100, and 200 mg·L$^{-1}$ paromomycin, respectively; WT=wild type (non-transformed) plant; L1, L2, and L3=leaf samples from three independent transformants.

(J) and (K) GUS expression (as shown by dark staining) in leaf tissue from a greenhouse-grown transgenic plant; surface and cross-section of the leaves, respectively. (L) GUS expression (dark staining) in root tissue of a young, in vitro-grown transgenic plant.

Figure 9:
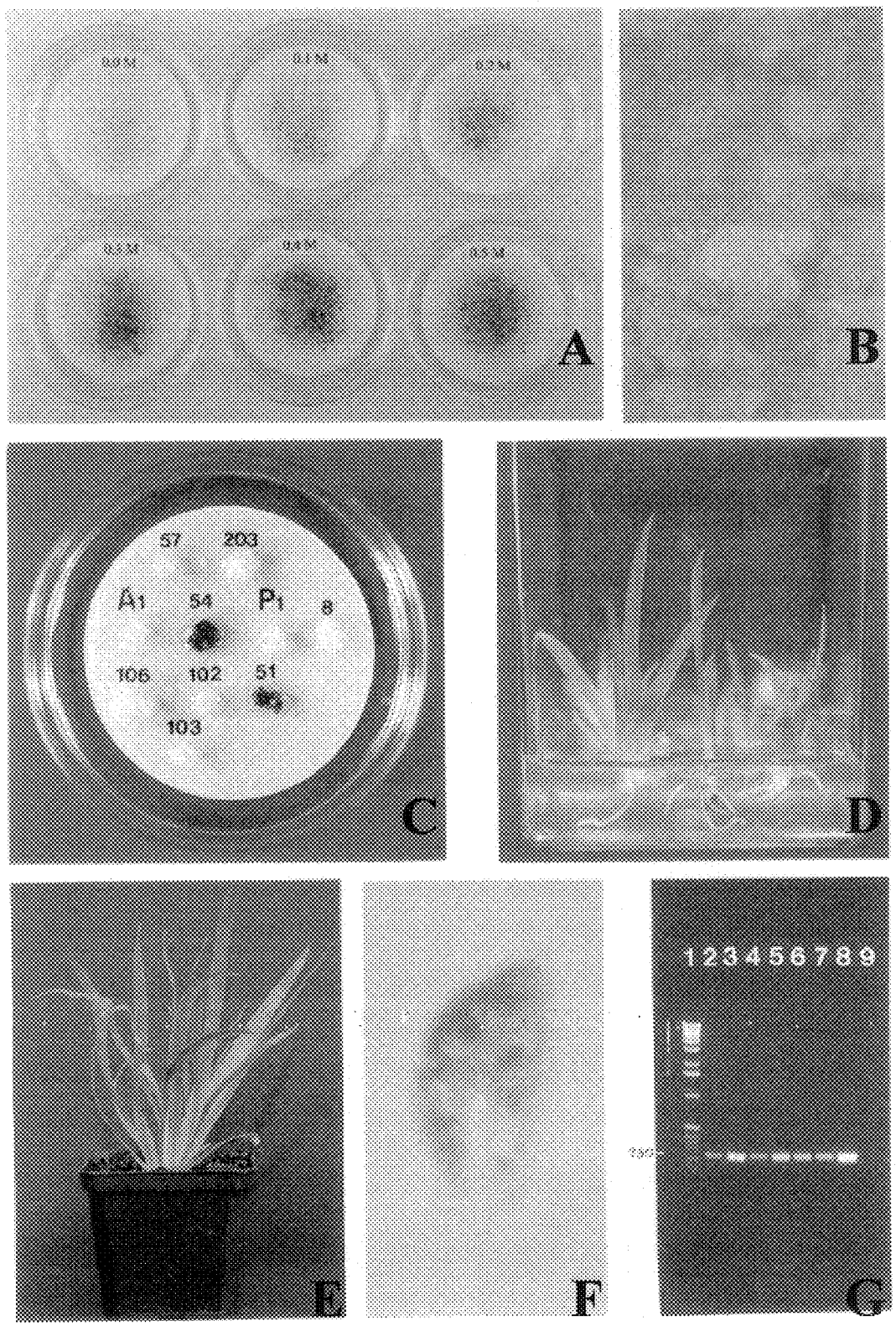

FIG. 9: Steps in biolistic transformation and regeneration of transgenic Iris plants.

(A) Effect of increasing concentrations of osmoticum (equimolar concentration of mannitol and sorbitol) on transient expression of the GUS gene 48 hours after transformation. (B) Several cell clumps that proliferated on selection medium (MS-C containing 10 mg Basta) about 2 weeks later.

(C) Stable transformation of callus lines #54 and #51 was confirmed by GUS staining several weeks later. (D) Regenerated #54 plants on MS-R medium.

(E) Plants derived from #54 transgenic line about 4 weeks after transfer to soil. (F) Staining of the leaf section for expression of the GUS gene. (G) Separation of a 250 bp fragment from the coding region of uidA (GUS) gene, amplified using PCR from genomic DNA of several independent transgenic plants, and separated by agarose electrophoresis. Key: lane 1–100 bp ladder; lane 2 contains transformant #51; lane 3, #52; lane 4, #57; lane 5, Z1; lane 6, Z10; lane 7, Z20; lane 8, a positive control; lane 9, a negative control (non-transformed plant).

DETAILED DESCRIPTION

I. Abbreviations and Definitions a. Abbreviations

*A. tumefaciens*: *Agrobacterium tumefaciens*

BA: 6-benzyladenin

Kin: kinetin

MS: Murashige and Skoog

NAA: 1-naphthaleneacetic acid b. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

cDNA (complementary DNA): A piece of DNA lacking internal, non-coding segments (introns) and regulatory sequences that determine transcription. cDNA is synthesized in the laboratory by reverse transcription from messenger RNA extracted from cells.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Plant: The term "plant" encompasses transformed plants, progeny of such transformed plants, and parts of plants, including reproductive units of a plant, fruit, flowers, seeds, etc. The transformation methods and compositions of the present invention are particularly useful for transformation of monocots, including ornamental monocots such as Iris species. Other species of monocotyledonous and dicotyledenous plants may also be transformed using the disclosed methods.

Purified: The term purified does not require absolute purity; rather, it is intended as a relative term. Thus, for example, a purified specific protein preparation is one in which the specific protein is more enriched than the protein is in its natural environment within a cell. Generally, a preparation of specific protein is purified such that the protein represents at least 5% of the total protein content of the preparation. For particular applications, higher purity may be desired, such that preparations in which the specific protein represents at least 25%, 50% or at least 90% of the total protein content may be employed.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Reproductive unit: A reproductive unit of a plant is any totipotent part or tissue of the plant from which one can obtain progeny of the plant, including, for example, seeds, cuttings, tubers, buds, bulbs, somatic embryos, microspores, and cultured cells (e.g., callus or suspension cultures).

Transformed; Transgenic: A cell, tissue, organ, or organism into which a foreign nucleic acid, such as a recombinant nucleic acid molecule (e.g., a recombinant vector), has been introduced is considered "transformed" or "transgenic," as is progeny thereof in which the foreign nucleic acid is present. A transformed tissue or plant may include some cells that are not transformed, i.e., may be chimeric, comprising transformed and untransformed cells. Such chimeric tissues may be used to regenerate transformed plants, and may be advantageous for this purpose since less in vitro propagation and selection will be required to produce chimeric tissues than tissues in which 100% of the cells are transformed. Regeneration of chimeric tissues generally will give rise to chimeric plants, i.e., plants comprised of transformed and non-transformed cells. Reproduction of these chimeric plants by asexual or sexual means may be employed to obtain plants entirely comprised of transformed cells.

As used herein, the term transformation encompasses all techniques by which a nucleic acid molecule (e.g., a recombinant nucleic acid molecule) might be introduced into such a cell, including transfection with viral vectors, transformation with plasmid vectors, and introduction of naked DNA by electroporation, lipofection, and particle gun acceleration.

In methods involving co-cultivation of plant cells (e.g., plant suspension or callus culture cells) with an Agrobacterium, the length of time necessary for co-cultivation is generally at least that length of time needed to transfer a complete T-DNA molecule from the bacterium to the plant cells. At a minimum, this is generally thought to be about 36 hours. However, to encourage higher efficiency transformation, usually the plant and bacteria cells will be co-cultivated for at least a48 hours. Additional time in co-cultivation may be appropriate in certain circumstances, such as at least 60 hours, at least 72 hours, or at least 84 hours. In one embodiment, Agrobacterium cells are incubated with plant cells, such as plant suspension or callus cells, for about 72 hours.

"Foreign" nucleic acids are nucleic acids that would not normally be present in the host cell, particularly nucleic acids that have been modified by recombinant DNA techniques. The term "foreign" nucleic acids also includes host genes that are placed under the control of a new promoter or terminator sequence, for example, by conventional techniques.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant nucleic acid is introduced by transformation is a transgenic plant, as are all offspring of that plant that contain the introduced transgene (whether produced sexually or asexually).

Vector: A nucleic acid molecule as introduced into a host cell, thereby producing a transformed host cell. A vector may include nucleic acid sequences that permit it to replicate in a host cell, such as an origin of replication. Such a construct preferably is a vector that includes sequences that are capable of transcription and translation of a polypeptide-encoding sequence in a given host cell (and may include a replication system, although some direct DNA introduction methods that have conventionally been used for monocot transformation do not require this). A vector may also include one or more selectable marker genes and other genetic elements known in the art.

For the practice of the present invention, conventional compositions and methods for preparing and using vectors and host cells are employed, as discussed, inter alia, in Sambrook et al. (*Molecular cloning: A laboratory manual.* 2nd ed. Cold Spring Harbor Laboratory Press, Plainview, N.Y., 1989), or Ausubel et al. (*In Current Protocols in Molecular Biology*, Greene Publishing Associates and Wiley-Intersciences, 1992).

II. General Discussion

The present invention provides methods of transforming and/or regenerating ornamental monocot plants, particularly irises, plants produced by these methods, and seeds and progeny of such plants. The methods of the present invention involve Agrobacterium-mediated transformation in which the transformation target cells are suspension-cultured monocot cells, for instance derived from young iris shoots. The present methods are useful in the production of transgenic monocots (e.g., irises) with altered and improved properties, and in the production of plants having selectable markers and proprietary tags.

A main objective was to establish an efficient and reproducible plant regeneration protocol from suspension-cultured cells of iris that would be suitable for genetic transformation, and to provide techniques for transformation of the iris cells, such as suspension-cultured cells.

a. Suspension Culture and Regeneration of Iris Cells

Suspension-cultured cells or cell aggregates can be induced to produce many plantlets in a short time. The use of suspension-cultured cells may be particularly beneficial in the in vitro culturing of monocots, in which in vitro plant regeneration generally has been more difficult than in dicots (Kamo et al., *In Vitro Cell Dev. Biol.*, 26:425–430, 1990; Wang and Nguyen, *Plant Cell Rep.*, 8:639–642,.1990). Plant regeneration from suspension-cultured cells generally involves four steps: initiation of friable callus; establishment of the suspension culture; induction of somatic embryogenesis or organogenesis; and shoot and root development. Optionally, cells in suspension culture can be transformed in order to produce transgenic plants upon regeneration.

Establishing cell suspension cultures is generally thought to be important because such cells generally have a higher capacity for plant regeneration (Ammirato, *Amer. J. Bot.*, 65 (Suppl.):89, 1978; Novak el al., *Bio/Technology*, 7:154–159, 1989; Tsukahara et al., *J. Plant Physiol.*, 149:157–162, 1996). Successful regeneration from suspension cells, however, has been reported only in a few ornamental monocots (Kamo et al., *In Vitro Cell Dev. Biol.*, 26:425–430, 1990; Shimizu et al., *Plant Cell Tiss. Org. Cult.* 50:27–31, 1997). The only prior report of iris plant regeneration from cell suspension culture indicated that the efficiency of this process was low (Shimizu et al., *Plant Cell Tiss. Org. Cult.* 50:27–31, 1997).

The present invention overcomes the limitations of prior work by optimizing Rax the cell culturing techniques, and in particularly is the surprising discovery that relatively old suspension cultures provide better cells for regeneration.

The inventors have developed protocols for efficient plant regeneration of, for instance, *Iris germanica L.* 'Skating Party,' from suspension cultures. Suspension cultures were maintained in Murashige and Skoog (MS) basal medium containing both an auxin and a cytokinin [for instance, 2,4-dichlorophenoxyacetic acid (2,4-D) and kinetin (Kin), respectively]. Suspension-cultured cells were transferred to a shoot induction medium containing lower amounts of an auxin and higher amounts of a cytokinin. Cell clusters that proliferated on this medium differentiated and developed shoots and plantlets in about five weeks. Regeneration apparently occurred via both somatic embryogenesis and shoot organogenesis.

Cell cluster size and plant growth regulator levels are significant factors influencing the efficiency with which suspension culture cells can be regenerated into whole plants. The highest regeneration rate for *Iris germanica* was achieved with cell clusters $\leq 280$ $\mu$m in diameter derived from suspension cultures grown for six weeks without subculturing in liquid medium. The liquid medium can contain, for instance, 5 $\mu$M 2,4-D and 0.5 $\mu$M Kin. Using these conditions, up to 4000 plantlets with normal vegetative growth and morphology can be generated from one gram of suspension-cultured cells in about 34 months.

Other levels of growth regulators sufficient and beneficial for regeneration of ornamental monocots (e.g., iris) from suspension culture include induction media containing 0.5 $\mu$M NAA and either 2.5 or 12.5 $\mu$M Kin. Developing medium containing 1.25 $\mu$M $N^6$-benzyladenine (BA) appears to be advantageously for high regeneration rates coupled with a high percentage of plantlets simultaneously developing shoots and roots. Rooted plantlets generated using the conditions described herein are easily acclimatized and transplanted to various soil mixtures, and can then be grown in a greenhouse. Under optimal conditions as many as 8000 plantlets could be regenerated from one gram cells in about four months.

In summary, optimal conditions for efficient in vitro plant regeneration from suspension-cultured cells of Iris include the following:
1) suspension-cultured cells should be grown in MS-L medium containing about 5 $\mu$M 2,4-D and about 0.5 $\mu$M Kin in the dark at 25° C. for about six weeks;
2) the cells should be passed through a 30-mesh stainless sieve to select cell clusters with diameter $\leq 520$ $\mu$m;
3) the screened cells should be inoculated onto MS-I medium containing about 2.5 to about 12.5 $\mu$M Kin and 0.0 to about 0.5 $\mu$M NAA, then cultured in the dark at 25° C. for about six weeks;
4) the differentiated clumps are then transferred to MS-D medium containing about 1.25 $\mu$M BA and incubated under light (about 50 $\mu$mol m$^{-2}$ s$^{-1}$) at 23° C. for about six weeks;

5) well-developed shoots and plantlets can then be transferred to MS-R medium for root initiation and development; and 6) the rooted plantlets are then transplanted to the greenhouse in a suitable substrate, such as a mixture containing one part each (by volume) peat moss, pumice, sandy loam.

b. Transformation of Iris Cells

With the provision herein of methods for the efficient in vitro culturing and regeneration of ornamental monocots such as irises, any gene of interest (more generally, any recombinant nucleic acid molecule) can be introduced to these plants to alter the phenotype of the resultant transgenic plant(s) (e.g., transgenic irises).

Three major approaches for plant transformation include *Agrobacterium tumefaciens*-mediated transformation, microprojectile bombardment (biolistic method), and direct gene transfer to protoplasts (electroporation and polyethylene glycol-mediated transformation). Microprojectile bombardment and direct gene transfer to protoplasts are used commonly to transform a variety of monocotyledonous plants (Vain, et al., *Biotechnol. Adv.*, 13:653–671, 1995). However, stable (integrative) transformation of only a few horticulturally important ornamental monocots, Cymbidium orchid (Yang et al., *Plant Cell Rpt.*, 18:978–984, 1999), Dendrobium orchid (Kuehnle and Sugii, *Plant Cell Rpt.*, 11:484–488, 1992), Phalaenopsis orchid (Anzai et al., *Plant Tis. Cult. Let.*, 13:265–272, 1996), and Gladiolus (Kamo et al., *J. Amer. Soc. Hort. Sci.*, 120:347–352, 1995), by microprojectile bombardment have been reported.

Agrobacterium-mediated transformation has certain advantages over other approaches such as integrating a few copies of T-DNA with defined border sequences and minimal rearrangement in the plant genome, preferential integration into transcriptionally active regions of the chromosome, high quality and fertility of resultant transgenic plants, and easy manipulation (Komari et al., *Plant Biotechnol.*, 1:161–165, 1998; Tingay et al., *Plant J.*, 11:1369–1375, 1997).

Methods for transforming dicotyledenous species with Agrobacterium are well established. In contrast, until recently monocotyledons were considered beyond the range of *A. tumefaciens* transformation methods. Various attempts to infect monocots with Agrobacterium were made in the 1970s and 1980s, but no conclusive evidence of integrative transformation was reported (Conner and Dommisse, *Intl. J. Plant. Sci.* 153:550–555, 1992; Smith and Hood, *Crop Sci.*, 35:301–309, 1995). Successful *A. tumefaciens*-mediated transformation, however, is now possible in several agronomically important monocots including corn (*Zea mays* L.), wheat (*Triticum aestivum* L.), rice (*Oryza sativa* L.), barley (*Hordeum vulgare* L.), and sugar cane (Saccharum spp. L.) (Arencibia et al., *Transgenic Res.*, 7:213–222, 1998; Cheng, et al., *Plant Physiol.*, 115:971–980, 1997; Hiei, et al., *Plant J.*, 6:271–282, 1994; Ishida, et al., *Nature Biotechnol.*, 14:745–750, 1996; Tingay, et al., *Plant J.*, 11:1369–1375, 1997). The utility of *A. tumefaciens* for stable (integrative) transformation of ornamental monocots has been demonstrated only in *Anthurium scherzerianum* Schott 'Rudolph' and 'UH1060' (Chen and Kuehnle, *J. Amer. Soc. Hort. Sci.*, 121:47–51, 1996), and Phalaenopsis orchid (Belarmino and Mii, *Plant Cell Rpt.*, 19:435–442, 2000).

Disclosed herein are methods for production of transgenic iris plants, particularly ornamental monocots such as Iris (e.g., *Iris germanica L.* 'Skating Party') from regenerable suspension cultures via Agrobacterium-mediated transformation and microparticle bombardment.

As described below (Examples 3 and 4), a series of selection agents were tested, and hygromycin and geneticin were identified as particularly suitable for selecting transformed iris cells. Suspension cultures of iris were co-cultured with *Agrobacterium tumefaciens* LBA 4404 (pTOK233). In the particular embodiment described, this Agrobacterium carried an intron-interrupted uidA (GUS) gene encoding β-glucuronidase, and hpt (hygromycin) and nptII (geneticin) selectable marker genes. Hygromycin- or geneticin-resistant calli having GUS enzyme activity were identified and treated as described below to induce plant regeneration. The methods described produced over 300 morphologically normal transgenic iris plants in about six months. About 80% of these transformants were GUS-positive and NPTII-positive (paromomycin-resistant). Integration of transgenes into the nuclear genome of iris plants was confirmed by Southern blot analysis.

In addition to these described steps, regeneration of transformed iris cells into transgenic plants can proceed by way of intermediate callus growth. In embodiments employing this intermediate step, transformed cells (e.g., transformed suspension culture cells) are incubated on callus induction medium with selection agent(s) prior to inducing shoot and/or root regeneration. The callus culture can be maintained in the laboratory for an extended period of time, and provides a continuous culture of transformed cells. This callus culturing step can also be used to expand the transformed culture size, thereby enabling production of a greater number of transformed plantlets upon induction of shoots/roots.

The provided transformation methods are efficient *A. tumefaciens*-mediated and microparticle-bombardment transformation systems for ornamental monocots such as *Iris germanica L.* Provision herein of these methods enables modification and improvement of horticulturally important ornamental monocots (e.g., irises) via genetic engineering.

c. Vector Construction, Choice of Promoters

A number of vectors suitable for stable transformation of plant cells or for the establishment of transgenic plants have been described in, e.g., Pouwels et al. (*Cloning Vectors: A Laboratory Manual*, 1985, Suppl., 1987), Weissbach and Weissbach (*Meth. Plant Mol. Bio.*, Academic Press, 1989) and Gelvin et al. (*Plant Molecular Biology Manual*, Kluwer Academic Publishers, 1990). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters useful for expressing genes in plant cells include, but are not limited to, the cauliflower mosaic virus (CaMV) 35S promoter, maize ubiquitin (Ubi-1) promoter, rice actin (Act) promoter, nopaline synthase promoter, and the octopine synthase promoter. A variety of plant gene promoters that are regulated in response to environmental, hormonal, chemical, and/or developmental signals also can be used for expression of foreign genes in plant cells, including promoters regulated by heat (e.g., heat shock promoters), light (e.g., pea rbcS-3A or maize rbcS promoters or chlorophyll a/b-binding protein promoter); phytohormones, such as abscisic acid; wounding (e.g., wunI); anaerobiosis (e.g., Adh); and chemicals such as methyl jasminate, salicylic acid, or safeners. It may also be advantageous to employ well-known organ-specific promoters such as endosperm-, embryo-, root-, phloem-, or trichome-specific promoters, for example.

A variety of plant gene promoters are regulated in response to environmental, hormonal, chemical, and/or developmental signals, and can be used for expression of the cDNA in plant cells. Such promoters include, for instance, those regulated by: (a) heat (Callis et al., *Plant Physiol.* 88:965, 1988; Ainley, et al., *Plant Mol. Biol.* 22:13–23, 1993; Gilmartin et al. *The Plant Cell* 4:839–949, 1992); (b) light (e.g., the pea rbcS-3A promoter, Kuhlemeier et al., *The Plant Cell*, 1:471–478, 1989, and the maize rbcS promoter, Schaffner and Sheen, *Plant Cell* 3:997, 1991); (c) hormones, such as abscisic acid (Marcotte et al., *Plant Cell* 1:969, 1989); (d) wounding (e.g., wuni, Siebertz et al., *Plant Cell* 1:961, 1989); and (e) chemicals such as methyl jasminate or salicylic acid (see Gatz et al., *Ann. Rev. Plant Physiol. Plant Mol. Biol.* 48:89–108 1997).

Alternatively, tissue specific (root, leaf, flower, or seed, for example) promoters (Carpenter et al., *The Plant Cell* 4:557–571, 1992, Denis et al., *Plant Physiol.* 101:1295–1304 1993, Opperman et al., *Science* 263:221–223, 1993, Stockhause et al., *The Plant Cell* 9:479–489, 1997; Roshal et al., *EMBO J.* 6:1155, 1987; Schernthaner et al., *EMBO J.* 7:1249, 1988; and Bustos et al., *Plant Cell* 1:839, 1989) can be fused to the coding sequence to obtained protein expression in specific organs.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin acetyltransferase or glyphosate) to facilitate manipulation in bacterial systems and to select for transformed plant cells.

Screenable markers are also used for plant cell transformation, including color markers such as genes encoding β-glucuronidase (gus) or anthocyanin production, or fluorescent markers such as genes encoding luciferase or green fluorescence protein (GFP).

d. Selection of Transformed Cells/Plants

Following transformation with the transformation vector, transformed cells are usually selected using a dominant selectable marker incorporated into the transformation vector. Typically, such a marker will confer antibiotic resistance on transformed cells, and selection of transformants can be accomplished by exposing the cells or seedlings derived from those cells to appropriate concentrations of the antibiotic. Alternatively, herbicide resistance genes/herbicides can be used in a similar manner. Specific examples of selection techniques are described below.

After transformed plants are selected and grown to maturity, they can be assayed to determine whether the desired recombinant gene has been stably integrated into the plant cells. Specific transgenes will require different assays to determine their presence. In addition to the test genes described herein, for instance, the integration of a gene that regulates flower color can be examined by measuring or otherwise determining flower color in the putative transgenic plant, and insect, pesticide or herbicide resistance genes can be tested by exposure to the appropriate challenge agent. Likewise, introduction of a gene that may alter (e.g., enhance) irone production can be assayed by measuring the presence of irones in the resultant transgenic plant bulbs. The effectiveness of transformation with other genes, for instance genes that enhance flower fragrance, or that increase flower longevity (e.g., cut flower longevity), can be examined by examining the trait being altered (floral fragrance and longevity, in these examples)

The invention is illustrated by the following non-limiting Examples.

EXAMPLES

Example 1

Efficient Plant Regeneration from Suspension-Cultured Cells of Tall Bearded Iris

Overview

A protocol was developed for efficient plant regeneration of *Iris germanica* L. 'Skating Party' from suspension cultures. Suspension cultures were maintained in Murashige and Skoog (MS) basal medium (pH 5.9) supplemented with 290 mg·L$^{-1}$ proline, 50 g·L$^{-1}$ sucrose, 5.0 µM 2,4-dichlorophenoxyacetic acid (2,4-D) and 0.5 µM kinetin (Kin). Suspension-cultured cells were transferred to a shoot induction medium [MS basal medium supplemented with 10 mg·L$^{-1}$ pantothenic acid, 4.5 mg·L$^{-1}$ nicotinic acid, 1.9 mg·L$^{-1}$ thiamine, 250 mg·L$^{-1}$ casein hydrolysate, 250 mg·L$^{-1}$ proline, 50 g·L$^{-1}$ sucrose, 2.0 g·L$^{-1}$ Phytagel, 0.5 µM 1-naphthaleneacetic acid (NAA), and 12.5 µM Kin]. Cell clusters that proliferated on this medium differentiated and developed shoots and plantlets in about 5 weeks. Regeneration apparently occurred via both somatic embryogenesis and shoot organogenesis. A series of experiments was conducted to optimize conditions during suspension culture to maximize subsequent plant regeneration. Parameters included 2,4-D and Kin concentrations, the subculture interval, and the size of cell clusters. The highest regeneration rate was achieved with cell clusters ≦280 µm in diameter, derived from suspension cultures grown for 6 weeks without subculturing in liquid medium containing 5 µM 2,4-D and 0.5 µM Kin. Up to 4000 plantlets with normal vegetative growth and morphology could be generated from 1 g of suspension-cultured cells in about 3–4 months.

Materials and Methods

Plant material and culture medium. Greenhouse-grown plants of *Iris germanica* 'Skating Party' were used as source material. Plants were grown in individual 4-L pots containing a 1:2:1 (v/v/v) mixture of peat: pumice: loam soil in a greenhouse at 25° C.±3° C./20° C.±3° C. (day/night) and a 16-hour photoperiod, with natural light supplemented by high-pressure sodium lamps (Energy Technics, York, Pa.) to give a PAR of 400–500 µmol m$^{-2}$ s$^{-1}$. Plants were fertilized with controlled release fertilizer Nutricot-Type 100 (N-P-K) (Plant Product Co. Ltd., Brampton, Ont., Canada) every 2–3 months. Each year, the plants were divided by splitting the rhizome and repotting in fresh soil mix. Media used for in vitro culture and plant regeneration are listed in Table 1.

TABLE 1

Media for in vitro iris culture and plant regeneration.

| Medium | Function | Composition |
| --- | --- | --- |
| MS-C | Callus induction and maintenance | MS basal medium (Sigma, # M5519), 290 mg · L$^{-1}$ proline, 50 g · L$^1$ sucrose, 5.0 μM 2,4-D, and 1.0 μM Kin, 3.0 g · L$^{-1}$ Phytagel, pH 5.9 |
| MS-L | Suspension culture maintenance | MS-C medium without Phytagel |
| MS-I | Shoot induction | MS basal medium, 250 mg · L$^{-1}$ proline, 250 mg · L$^{-1}$ casein hydrolysate, 10 mg · L$^{-1}$ pantothenic acid, 4.5 mg · L$^{-1}$ niacin, 1.9 mg · L$^{-1}$ thiamin, 50 g · L$^{-1}$ sucrose, 2.0 g · L$^{-1}$ Phytagel, Kin$^z$ and NAA$^z$, pH 5.7 |
| MS-D | Shoot elongation and development | MS-I medium without Kin and NAA supplemented with BA$^z$ |
| MS-R | Rooting and development of plantlets | MS-1 medium without growth regulators |

$^z$Specific concentrations of Kin, NAA, and BA are given in the text.

Establishment and maintenance of suspension cultures. Newly sprouted shoots (≈40 to 50 mm tall) were excised from the stock plants and used for callus induction. Two to three of the outermost leaves were removed from each shoot. The basal portions were excised and washed thoroughly with tap water, immersed in 75% ethanol for one minute, then in 1% sodium hypochlorite containing Tween 20 (2 to 3 drops/100 mL). They were gently shaken on a rotary shaker (100 rpm) for 25 min, and then rinsed three times with sterile water. The basal portion of each leaf was carefully separated from the shoot and sliced into approximately 5-mm-thick pieces. The explants were placed on MS-C medium (Table 1) to induce callus development. Calli were cultured in the dark at 25° C. and subcultured every three weeks on the same type of medium.

To establish suspension cultures, about 1 g of callus tissue was transferred to each 250-mL Erlenmeyer flask containing 75 mL of MS-L medium (Table 1), incubated in the dark at 23° C. on a rotary shaker at 100 rpm, and subcultured monthly.

Plant regeneration. Six-week-old suspension cultures were filtered through a 30 mesh stainless screen (Sigma, Chem. Co., St. Louis, Mo.) to remove large cell aggregates. The pass-through fraction was collected in 50-mL sterile tubes and centrifuged at 2500 g$_n$ for five minutes in a clinical centrifuge (HN-SII, International Equipment Co., Needham Heights, Mass.). The pelleted cells were weighed and resuspended in MS-I medium (Table 1) without Phytagel at 0.2 g·mL$^{-1}$ final density. A 0.5-mL aliquot was inoculated onto each 15 mm×60 mm sterile plastic plate containing 20 mL of solid MS-I medium to induce somatic embryogenesis. The plates were incubated in the dark at 25° C. for five weeks.

The clumps of induced structures were transferred to Magenta GA-7 vessels (Sigma) containing 50 mL of MS-D medium (Table 1). Clumps were cultured at 23° C. under light (≈50 μmol m$^{-2}$ s$^{-1}$ for 16 hour/24 hour) for six weeks for shoot elongation and development. Clumps of well-developed shoots with or without roots were transferred to MS-R medium (Table 1) for induction and further development of roots under the same conditions for five more weeks. Plantlets were transferred to a soil mix (1:1:1 peat: perlite: sandy loam, v/v/v) in 1.5-L pots and acclimatized on a mist bench (Relative Humidity 95–98%) in the greenhouse. After four weeks, they were transferred to a bench without mist and fertilized with Nutricot-Type 100 controlled-release fertilizer.

Effects of 2.4-D and kinetin. Twenty combinations of 2,4-D (0.0, 1.0, 5.0, 25.0, and 125.0 μM) and Kin (0.0, 0.5, 2.5, and 12.5 μM) in MS-L medium were tested. Two grams of suspension tissue were inoculated into each 250-mL Erlenmeyer flask containing 50-mL of medium supplemented with various combinations of 2,4-D and Kin and incubated for six weeks. The cultures were then inoculated onto MS-I medium to induce plant regeneration as above. The numbers of differentiated and regenerable clumps were determined and expressed as numbers of clumps/g cells. The effect of different combinations of 2,4-D and Kin on synchronous development of shoots and roots was scored five weeks after the differentiated clumps were transferred to MS-D medium.

Effect of subculture interval. Suspension cultures used for this test were continuously incubated in MS-L medium for up to nine weeks without being subcultured. Samples were removed weekly from Week 4 to Week 9 and subjected to all the steps in our general procedure for plant regeneration. The numbers of differentiated and regenerable clumps were determined and expressed as numbers of clumps/g cells.

Effect of size of cell clusters. Six-week-old suspension cultures were subsequently screened through a series of five different sized stainless sieves (Sigma) including mesh sizes 10 (1910 μm), 20 (860 μm), 30 (520 μm), 40 (380 μm), and 50 (280 μm). (Pore size of a particular mesh sieve is given in parentheses). Each fraction retained on a screen was collected separately and assigned the number of the corresponding mesh size. All the cells passing through the 50-mesh sieve were collected and designated as P50. The largest cell aggregates, retained on the 10-mesh sieve, were discarded, because in preliminary experiments cell aggregates ≧2 mm diameter exhibited low regeneration capability, Each fraction was weighed and resuspended in MS-I medium without Phytagel at 0.2 g·mL$^{-1}$ final density. A 0.5-mL aliquot of each fraction was inoculated on each of five replicate plates (15 mm×60 mm) of solid MS-I medium. Plant regeneration was carried out a s outlined above, and the numbers of differentiated and regenerable clumps were determined and expressed as numbers of clumps/g cells.

Scanning electron microscopy (SEM). Samples from several different stages of differentiation were excised from tissues grown on MS-I medium and fixed overnight at 4° C. in 2% glutaraldehyde in 0.05 M sodium phosphate buffer, pH 7.2. Samples were washed in the same buffer without glutaraldehyde for about 2 hours and dehydrated with a graded ethanol series. Samples were dried in a CPD 020 critical point dryer (Balzers Union, Liechtenstein) and mounted on either 'Spot-o-glue' adhesive tabs (Avery, Azusa, Calif.) or conductive carbon tabs (Ted Pella, Redding, Calif.) on SEM stabs. Samples were coated with gold:palladium (60:40, w/w) in an Edwards S150B sputter coater (Crawley , England) and examined with a scanning electron microscope (3300FE, Amray, Bedford, Mass.). Data collection and analysis. In all experiments concerning suspension cultures, the data were expressed as the number of differentiated clumps per gram cells on MS-I medium. Data were collected and processed for each of five duplicated plates, and each entire experiment was repeated three times. At the developing stage, 15 to 30 differentiated clumps or regenerable clumps were transferred to three to six GA-7 Magenta vessels containing MS-D medium. We counted the number of differentiated clumps per gram tissue and the number of regenerable clumps that developed both shoots and roots or shoots only on the MS-D medium. The data were subjected to analysis of variance (ANOVA) and Duncan's multiple range test ($P \leq 0.05$).

Results

Establishment and maintenance of suspension cultures. The callus induction rate was investigated six weeks after the leaf pieces were placed on MS-C medium. Callus induction capabilities of different leaf positions differed greatly. The highest rate of callus induction (>80%) was from the 2 cm basal portions of the two innermost leaves. Two types of induced calli, i.e., compact and friable, were identified. Initially, both types of calli were used to establish suspension cultures. When friable calli were inoculated into the MS-L medium, they developed into dispersible cell aggregates after two to three subcultures. Stable suspension cultures were successfully established after three to five subcultures and were maintained by subculturing every three weeks in the same medium. Compact calli were unsuitable for production of suspension culture, however, because they grew and separated into large clumps in the MS-L medium even after repeated subculturing.

Morphogenesis of plant regeneration. To verify the morphogenic process of plant regeneration from the suspension cultures, cells collected by centrifugation were placed on the MS-I medium and incubated for up to five weeks. The morphogenesis of these cultures was recorded weekly. Initiation and development of differentiated structures did not occur synchronously. When the suspension cultures were inoculated onto the solid MS-I medium, they appeared as irregular, multicellular aggregates, containing from several to hundreds of cells. A few days to two weeks after being placed on the MS-I medium, the cell aggregates began to enlarge. After about two weeks, the first visually identifiable opaque calli had formed. Close examination of those structures by SEM revealed the formation of a large number of globular nodules. One to two weeks later, some of the calli underwent further growth and differentiation and appeared as independent, white, globular structures closely resembling globular embryos. Soon thereafter, the majority of globular embryo-like structures started to elongate and in the next few weeks differentiated into shoot apices. However, few or no roots developed at this time, and many of those that did develop were not directly connected to developing shoots. When those structures were transferred to the MS-D medium containing 1.25 $\mu$M 6-benzyladenin (BA), 80–90% developed into plantlets with or without roots. Both shoots and plantlets were transferred to MS-R medium to facilitate root differentiation and development. The majority of shoots developed roots within five weeks. After five weeks on MS-R medium there were no apparent differences in either size or development stage between newly rooted shoots and those plantlets that had already developed both shoots and roots on the MS-D medium. The number of regenerated shoots ranged from 15 to 20 shoots per clump. Regenerated plants were eventually transferred to pots containing soil mix, and were readily acclimatized under greenhouse conditions.

Figure 1:
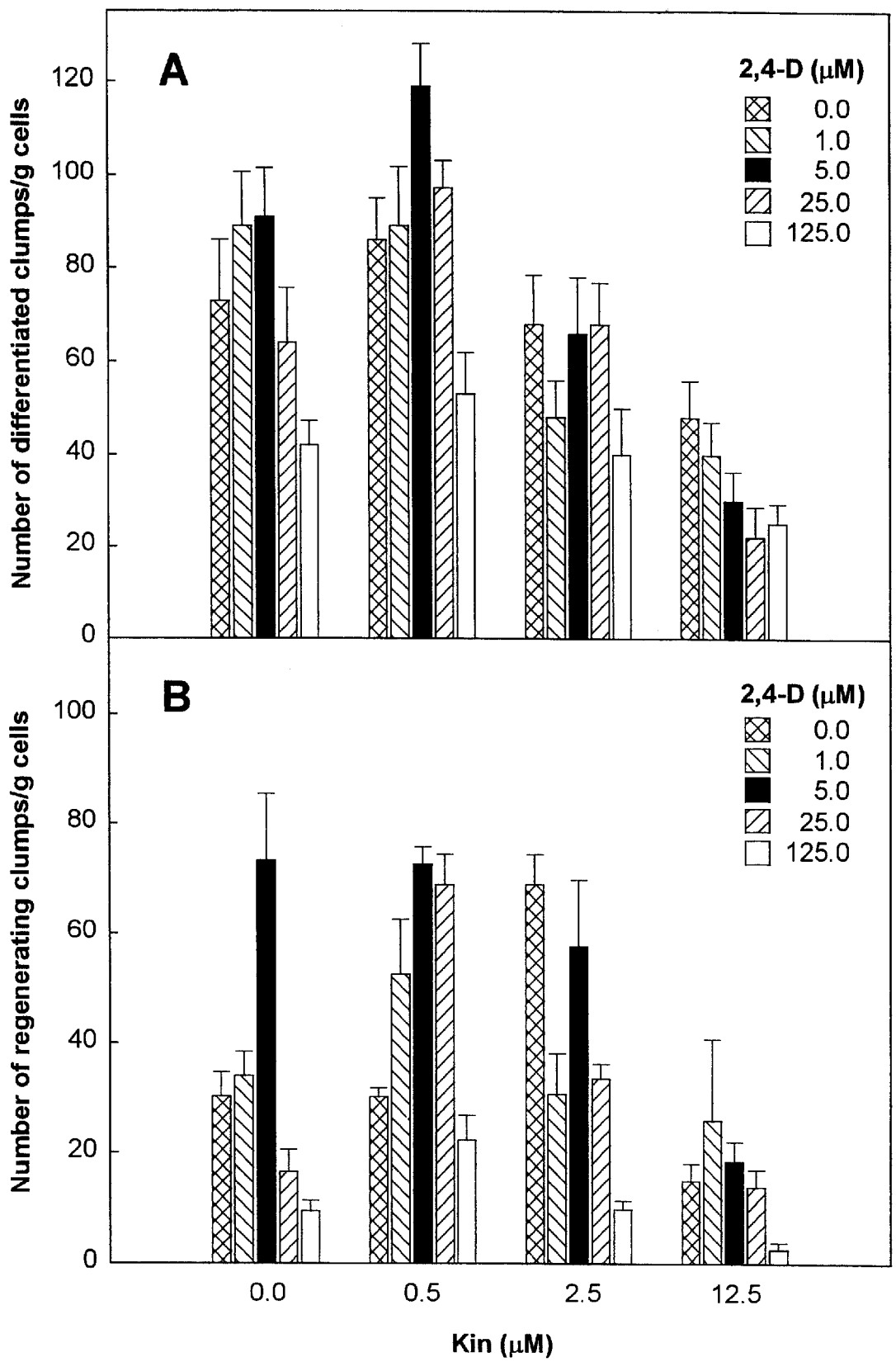
FIG. 1: Effects of 2,4-D and Kin combinations in MS-L medium on (A) number of differentiated clumps/g cells five weeks after suspension-cultured iris cells were transferred to the MS-I medium, and (B) number of regenerable clumps/g cells five weeks after differentiated clumps were transferred to MS-D medium. Bars represent standard errors of the means, n=15.
Figure 2:
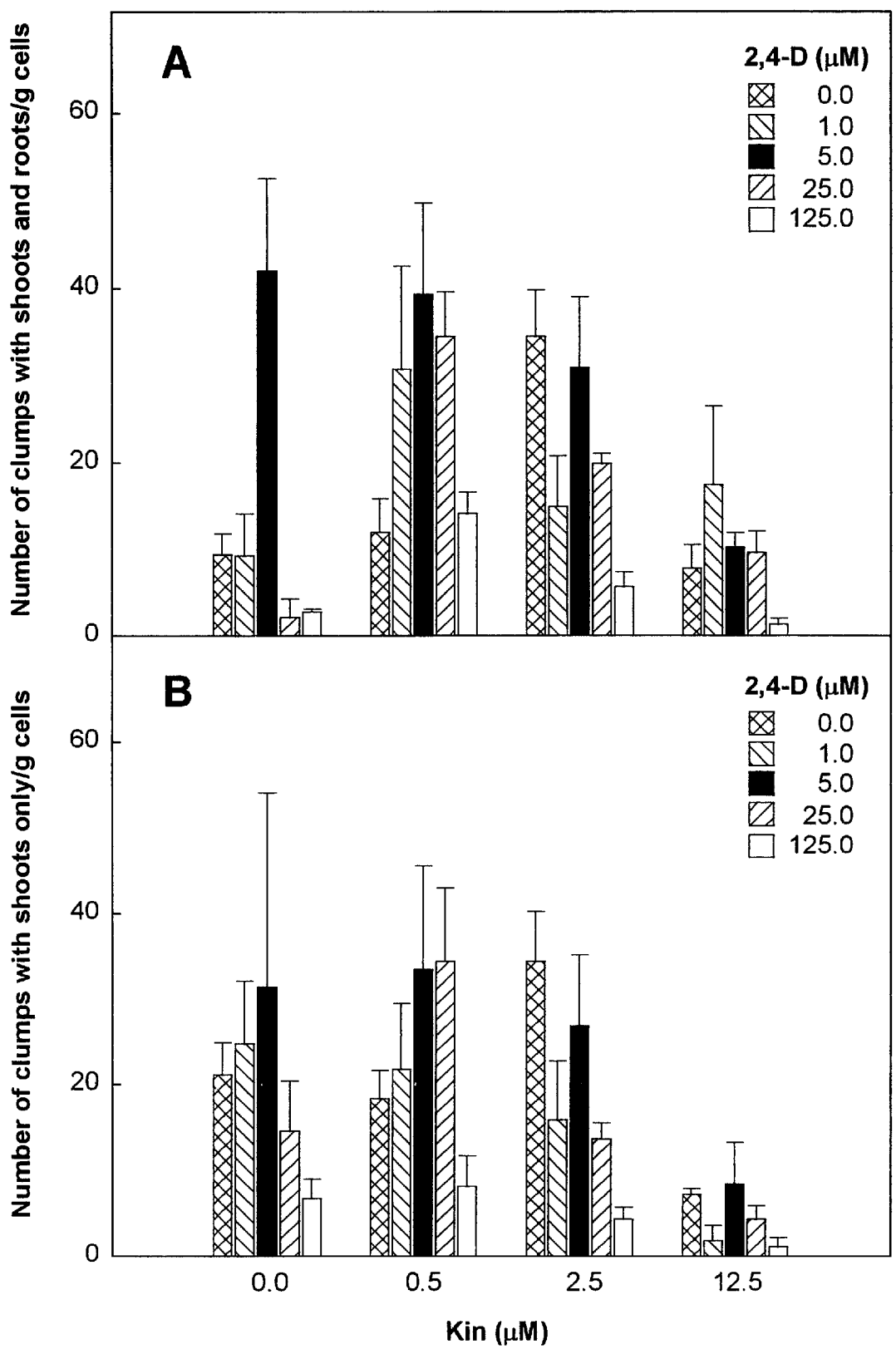
FIG. 2: Effects of 2,4-D and Kin combinations in MS-L medium on differentiation of shoots and roots from iris cell suspension culture. Number of regenerable clumps/g cells that developed both shoots and roots (A), and number of regenerable clumps/g cells that developed shoots only (B) five weeks after differentiated clumps were transferred to MS-D medium. Bars represent standard errors of the means, n=15.

Effects of 2,4-D and kin combinations. Among the various 2,4-D and Kin combinations, the MS-L medium containing 5.0 $\mu$M 2,4-D and 0.5 $\mu$M Kin promoted significantly more differentiated clumps ($P \leq 0.05$), than did other media, and these clumps produced single or joined induced structures (FIG. 1A). MS-L medium with 0.5 $\mu$M Kin in combination with all evaluated concentrations of 2,4-D generally gave rise to the best differentiation (FIG. 1A). The MS-L medium with 5.0 $\mu$M 2,4-D in combination with 0.5 $\mu$M Kin or without Kin consistently yielded the most regenerable clumps, i.e., the clumps that survived the transfer from MS-I to MS-D medium and subsequently developed into shoots or plantlets (FIG. 1B). Cells grown in MS-L medium containing 5.0 $\mu$M 2,4-D consistently developed both shoots anci roots simultaneously during the regeneration process (FIG. 2A). The same level of 2,4-D in MS-I medium enhanced subsequent shoot development on MS-D medium (FIG. 2B). Analysis of variance for plant regeneration showed that main effects of both Kin and 2,4-D were highly significant ($P \leq 0.01$).

Interaction of Kin and 2,4-D was also significant for three of the four measured responses (Table 2, Parts I and II).

TABLE 2

Mean squares from the analysis of variance for four parameters associated with plant regeneration from suspension cultured cells of Iris as a result of growth on media supplemented with Kin and 2,4-D in a 4 × 5 factorial experiment.

| Source of variation | df | No. differentiated clumps | No. regenerating clumps | No. clumps with shoots and roots | No. clumps with shoots only |
| --- | --- | --- | --- | --- | --- |
| Kin | 3 | 8574** | 2534** | 732** | 1052** |
| 2,4-D | 4 | 2193** | 3210** | 1057** | 605** |
| Kin × 2,4-D | 12 | 502* | 506** | 206* | 78$^{NS}$ |
| Error | 40 | 249 | 105 | 101 | 167 |

Symbol Key:
Non-significant ($^{NS}$), or significant at $P \leq 0.05$ (*) or 0.01 (**).

Figure 3:
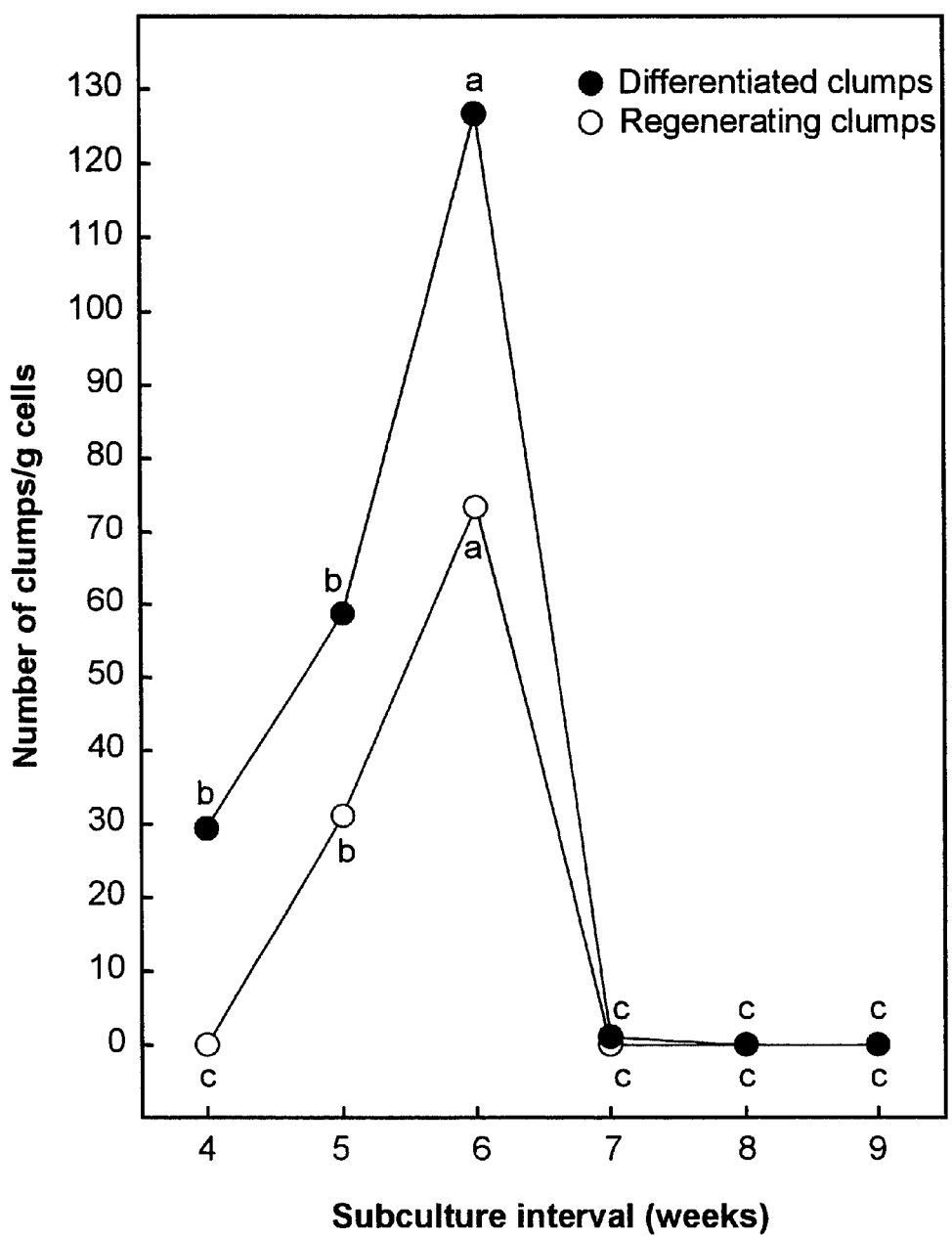
FIG. 3: Effect of subculture interval on number of differentiated clumps/g cells 5 weeks after suspension-cultured cells of iris were transferred to MS-I medium (A), and number of regenerable clumps/g cells five weeks after the differentiated clumps were transferred to MS-D medium (B). Data points within the same clump type followed by different letters are significantly different (P$\leq$0.05) according to Duncan's multiple range test (n=15).
Figure 4:
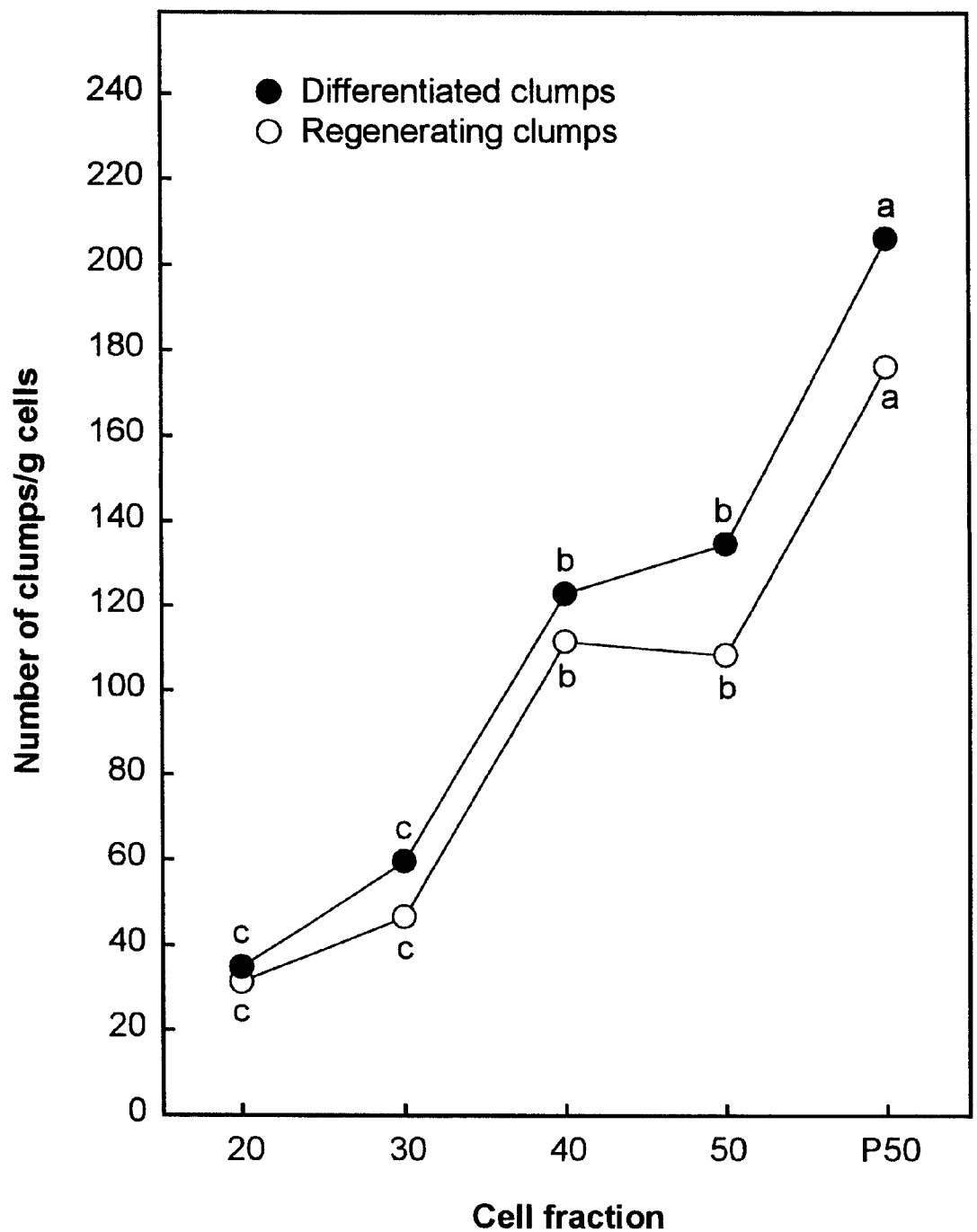
FIG. 4: Effect of the size of multicellular aggregates in suspension cultures on plant regeneration. Number of differentiated clumps/g cells 5 weeks after suspension-cultured cells were transferred to MS-I medium (A), and number of regenerable clumps/g cells 5 weeks after the differentiated clumps were transferred to MS-D medium (B). Each cell fraction retained on a particular sieve was assigned the number of the corresponding mesh size [20 mesh (860 $\mu$m), 30 mesh (520 $\mu$m), 40 mesh (380 $\mu$m), and 50 mesh (280 $\mu$m)]. The cell fraction passing through the 50 mesh sieve ($\leq$280 $\mu$m) was designated as P50. Within clump type, data points followed by different letters are significantly different (P$\leq$0.05) according to Duncan's multiple range test (n=15).

Effect of subculture interval. Suspension cells collected from cultures maintained for six weeks without subculturing consistently developed the most differentiated clumps per gram tissue on MS-I medium (FIG. 3). Many differentiated clumps derived from the six-week-old cultures survived the transfer from MS-I to MS-D medium, and grew into healthy shoots or plantlets. Such clumps are referred to as 'regenerable clumps.' However, when cells were collected from suspension cultures maintained in the MS-L medium for less than six weeks, the numbers of both differentiated and regenerable clumps were dramatically lower. Suspension cells collected from suspension cultures maintained for more than seven weeks without subculturing failed to regenerate. Effect of size of cell clusters. The numbers of both differentiated clumps and regenerable clumps per gram tissue strongly depended on the size of cell aggregates found in the suspension cultures (FIG. 4). The smaller the cell clusters, the higher the numbers of both clump types obtained. Cell fractions passing through the 30-mesh sieve (fractions 40, 50, and P50) generally produced more of both differentiated and regenerable clumps. The fraction passing through the 50-mesh sieve (fraction P50) produced the greatest numbers of both differentiated clumps and regenerable clumps per gram tissue.

Discussion

Friable calli are usually considered a prerequisite for establishing cell suspension cultures. Lu and Vasil (*Ann. Bot.*, 48:543–548, 1981) and Vasil and Vasil (*Amer. J. Bot.*, 69:1441–1450, 1982), however, established suspension cultures from compact calli of *Panicum maximum* Jacq. and *Pennisetum americanum* K. Schum., respectively. Surprisingly, in the current study, cell suspension cultures of *I. germanica* were established only from friable calli.

Generally callus or cell suspension cultures are capable of organogenesis, embryogenesis, or both, when first initiated. They gradually lose morphogenic ability when maintained by subculturing on a medium that enables continuous growth. This decline in morphogenic ability may result from changes in the nucleus (Mitra et al., *Amer. J. Bot.*, 47:357–368, 1960; Smith, and Street, *Ann. Bot.*, 38:223–241, 1974; Torrey, *Science*, 128:1148, 1958; Torrey, *Physiol. Plant.*, 20:265–275, 1967) or physiological changes (Reinert and Backs, *Nature*, 220:1340–1341, 1968; Reinert et al., *Les Culture de Tissus de Plantes*, Colloq. Intern. No. 193: 261–268, Centre Natl. Res. Sci., Strasbourg, France, 1970; Steward, *Phytomorphology*, 17:469–507, 1967; Sussex and Frei, *Phytomorphology*, 18:339–349, 1968; Syono, *Plant Cell Physiol.*, 6:403–419, 1965). However, suspension cultures from Iris germanica 'Skating Party' maintained for more than 3 years via repeated subculture as described herein still demonstrated high regeneration capacity. Furthermore, there were few grossly aberrant phenotypes (<1%) among more than 500 regenerated plants. Plants with aberrant phenotypes had yellow or white streaking on leaves and a few plants were slow growing.

In vitro regeneration of iris was assumed to be via somatic embryogenesis (Jéhan et al., *Plant Cell Rep.*, 13:671–675, 1994; Laublin et al., *Plant Cell Tiss. Org. Cult.*, 27:15–21, 1991; Radojević et al., *Acta Hort.*, 212:719–723, 1987; Shimizu et al., *Plant Cell Tiss. Org. Cult.* 50:27–31, 1997; Shimizu et al., *Euphytica*, 89:223–227, 1996). However, in a detailed anatomical study of Iris setosa Pall. ex Link., Radojević and Subotić (*J. Plant Physiol.*, 139:690–696, 1992) demonstrated both somatic embryogenesis and organogenesis. In the current study, suspension-cultured cells differentiated many globular nodules 2–3 weeks after transfer to MS-I medium and then developed globular embryo-like structures. Further morphogenesis of globular structures on MS-D medium seemed to be via both somatic embryogenesis and organogenesis.

The efficiency of regeneration from suspension-cultured iris cells using the herein-described technique was much higher than that reported from in vitro callus culture of iris on solid media (Fujino et al., *J. Jpn. Soc. Hort. Sci.*, 41:66–71, 1972; Gozu et al., 13:12–16, 1993; Hussey, *Scientia Hort.*, 4:163–165, 1976; Jéhan et al., *Plant Cell Rep.*, 13:671–675, 1994; Laublin et al., *Plant Cell Tiss. Org. Cult.*, 27:15–21, 1991; Meyer et al., *HortScience*, 10:479–480, 1975; Radojević and Landre, *Proc. 7th Intern. Congr. Plant Tissue and Cell Culture*, Amsterdam, The Netherlands, (Abstr.) B4–100, 1990; Radojević et al., *Acta Hort.*, 212:719–723, 1987; Radojević and Subotić, *J. Plant Physiol.*, 139:690–696, 1992; Reuther, *Ber. Deutsch Bot. Ges.*, 90: 417–437, 1977; van der Linde et al., *Acta Hort.* 226:121–128, 1988; Yabuya et al., *Euphytica* 57:77–81, 1991). Shimizu et al. reported plant regeneration frequency of about 36 shoots/20 mg of suspension-cultured cells (*Plant Cell Tiss. Org. Cult.* 50:27–31, 1997). Under optimal conditions, the disclosed method produces about 4000 iris plantlets per gram of screened cells, or about two-fold above that reported by Shimizu et al. (*Plant Cell Tiss. Org. Cult.* 50:27–31, 1997). This is based on ≈180 regenerable clumps per gram cells (FIG. 4) and about 15–20 shoots/clump. To date, this represents the most efficient regeneration system of iris plants from suspension-cultured cells. This system allows mass propagation of desirable iris genotypes and makes genetic transformation possible.

Growth regulators exerted the most critical influence on plant regeneration from iris suspension cultures. Plant growth regulators in the MS-L medium affected subsequent regeneration. Cells from the MS-L medium containing 5.0 $\mu$M 2,4-D and 0.5 $\mu$M Kin produced the most differentiated clumps (FIG. 1A). Differentiated clumps from suspension-cultured cells grown in MS-L medium with 5.0 $\mu$M 2,4-D and either 2.5 $\mu$M Kin or without Kin had the best survival rates. Differentiated clumps from MS-L medium with 5.0 $\mu$M 2,4-D and either 0 or 2.5 $\mu$M Kin were most likely to develop plantlets after transfer from MS-I to MS-D medium (FIG. 1B). A ratio of about 10:1 (2,4-D:Kin) in the culture medium considerably enhanced regenerable callus formation of iris on agar medium. One specific example is 5.0 $\mu$M 2,4-D and 0.5 $\mu$M Kin (10:1).

In the current study, cell clumps showed progressively higher regeneration potentials as sieve size decreased (FIG. 4). The highest regeneration rate was obtained from the fraction comprised of small cell aggregates ≦280 $\mu$m (passing through a 50-mesh sieve). In other species, cells in smaller-sized clumps generally had very dense cytoplasm resembling embryogenic cell lines (Halperin, *Amer. J. Bot.*, 53:443–453, 1966). The larger the clumps, the more difficult it may be for the majority of the cells to respond to the inductive stimuli for morphogenesis. The physiological state of the larger clumps might not be suitable for regeneration. In contrast, clumps ≦190 $\mu$m also demonstrated low regeneration. If the cell aggregates were too small, they could not reach the required size and regeneration could not proceed. Even in the appropriate physiological (regeneration-competent) state, only limited numbers of single cells can accommodate the changes if dissociated from the cell mass. Though the exact mechanism is unknown, the size of multicellular aggregates in suspension culture appears to be an important factor affecting regeneration efficiency.

The interval for subculturing of suspension cultures depends on the plant genotype, and usually ranges from one to four weeks (Kamo et al., *In Vitro Cell Dev. Biol.*, 26:425–430, 1990; Shimizu et al., *Euphytica*, 89:223–227, 1996; Wang and Nguyen, *Plant Cell Rep.*, 8:639–642, 1990). Almost all research on regeneration from suspension-cultured cells has focused on the type and concentration of growth regulators, medium composition, and culture conditions; there are no reports on the influence of the length of the subculture interval on regeneration efficiency from iris suspension culture. The most important finding in the present study may be that the length of the subculture interval had a remarkable effect on plant regeneration in *Iris germanica* 'Skating Party.' The subculture interval for regular maintenance of suspension-cultured cells was three to four weeks. If extended to five weeks, most cells or cell aggregates became necrotic soon after transfer to fresh MS-L medium. If, however, the cultures were kept intact in the same vessel for six to seven weeks without subculturing, they were still recoverable and gave rise to the highest regeneration after transfer to MS-I medium. Beyond this period, both recovery and regeneration rates were sharply reduced. Cells in suspension cultures vary in physiological status over time and this is closely associated with regeneration competency.

Example 2

Improved Plant Regeneration from Suspension-Cultured Cells of *Iris germanica* L. 'Skating Party'

Overview

To improve the efficiency of iris plant regeneration, we tested the influence of several combinations of kinetin (Kin) and 1-naphthaleneacetic acid (NAA) in culture media on the induction of morphogenesis and the subsequent development of plantlets. The highest rates of regeneration (67%) were consistently observed in induction media containing 0.5 $\mu$M NAA and either 2.5 or 12.5 $\mu$M Kin. Developing medium containing 1.25 $\mu$M N$^6$-benzyladenine (BA) was optimal for high regeneration rates and a high percentage of plantlets simultaneously developing shoots and roots. Rooted plantlets were easily acclimatized and transplanted to various soil mixtures, then grown in the greenhouse. Under optimal conditions as many as 8000 plantlets could be regenerated from one gram cells in about four months.

Materials and Methods

Iris suspension cultures and media. Suspension cultures of *Iris germanica* 'Skating Party' established from friable calli (established as described in Example 1) were maintained in MS-L medium (Table 1) in the dark on a gyrating shaker (100 rpm) at 23° C. They were subcultured every three weeks (unless otherwise described), by decanting MS-L medium and transferring the cells into two 250-mL flasks, each containing 75 mL of MS-L medium.

Preparation of suspension cultures for plant regeneration. For regeneration experiments, suspension cultures were prepared as described in Example 1. Six-week-old cultures were screened through a 30-mesh stainless sieve. The pass-through fraction (containing cell clusters $\leq$520 $\mu$m in diameter) was collected in 50-mL tubes and centrifuged at 1000 $g_n$ for 10 minutes in a clinical centrifuge (HN-SII; International Equipment Co., Needham Heights, Mass.). The pelleted cells were weighed and resuspended in a liquid MS-I medium (Table 1) at 0.2 g·mL$^{-1}$ final density.

Effect of Kin and NAA, a/one and in combination, in MS-I medium. To induce plant morphogenesis from suspension-cultured cells, 16 different combinations of NAA (0.0, 0.5, 2.5, and 12.5 $\mu$M) and Kin (0.0, 2.5, 12.5, and 62.5 $\mu$M) were evaluated. A 0.5-mL aliquot of the resuspended cells was inoculated on each 15×60 mm plastic plate containing 20 mL MS-I medium with different combinations of Kin and NAA. The cells were spread with a spoon-like spatula to form a uniform layer on the surface of MS-I medium. The plates were sealed with Parafilm® and incubated in the dark at 25° C. The number of differentiated clumps was recorded after five weeks. The clumps were collected and grouped into four size classes: large (>10 mm), medium (5 to 10 mm), small (2 to 5 mm) and very small (<2 mm).

The regeneration potential of differentiated clumps was assessed by randomly sampling 30 to 60 clumps from each size class and transferring them to three to six Magenta GA-7 vessels (Sigma Chem. Co., St. Louis, Mo.) containing 50 mL of MS-D medium (Table 1) supplemented with 1.25 $\mu$M BA. They were then incubated under light (50 $\mu$mol m$^{-2}$ s$^{-1}$) at 23° C. for six weeks. The total number of regenerating clumps (i.e., differentiated clumps that continued to grow and develop on MS-D medium) was counted, and percentages of regenerating clumps that developed shoots only or plantlets (rooted shoots derived from somatic embryos) were recorded. The regenerated shoots and plantlets were transferred to MS-R medium (Table 1) to promote root development. Each Kin/NAA combination was evaluated in five plates per experiment; the entire experiment was repeated three times.

Effect of BA concentration in MS-D medium. Several concentrations of BA in MS-D media were evaluated for their effects on further growth and development of randomly sampled differentiated clumps from the MS-I medium containing 2.5 $\mu$M Kin and 0.5 $\mu$M NAA. At the developing stage, 15 to 21 differentiated clumps were transferred to three to six Magenta GA-7 vessels containing 50 mL MS-D medium supplemented with 0.0, 1.25 or 2.5 $\mu$M BA. The clumps were incubated under light (50 $\mu$mol m$^{-2}$ s$^{-1}$) at 23° C. for six weeks. The experiment was repeated three times.

The numbers of regenerating clumps that developed shoots only or plantlets were recorded and expressed as percentages of the total number of regenerating clumps. The effect of BA concentration on growth and development of shoots and plantlets was assessed by measuring the length of the shoots.

Relationship between size and age of differentiated clumps and their regeneration potential. To determine the optimal period to maintain clumps, we inoculated the screened cells onto MS-I medium containing 2.5 $\mu$M Kin and 0.5 $\mu$M NAA, then incubated them in the dark at 25° C. for 5 weeks. The differentiated clumps were collected and grouped into the four size classes described earlier. The number of clumps in each class was recorded and the clumps were placed back onto the same MS-I medium. They were continuously cultured under the same conditions for another 4 weeks. Changes in size and distribution of differentiated clumps in each size class were recorded weekly. Every week 45 clumps from each class were transferred to Magenta GA-7 vessels (15 clumps per vessel) containing 50 mL MS-D medium with 1.25 $\mu$M BA, then incubated under light (50 $\mu$mol m$^{-2}$ s$^{-1}$) at 23° C. After six weeks, the regeneration potential (%) and the percentage of clumps that developed large shoots (>3 cm long) were recorded for each size class.

Effects of potting substrates and acclimatization conditions on survival and growth of plantlets in the greenhouse. Rooted plantlets were cultured for six weeks on MS-R media, then transferred to 1.5-L pots in the greenhouse. The eight substrates tested were: peat moss; perlite; sandy loam; peat moss, sandy loam (1:1, v/v); peat moss, perlite (1:1, v/v); perlite, sandy loam (1:1, v/v); peat moss, perlite, sandy loam (1:1:1, v/v/v); and peat moss, pumice, sandy loam (1:1:1, v/v/v). Forty plantlets (eight pots×five plantlets per pot) were tested in each substrate with 20 plantlets per group. One group was maintained on a mist bench, with relative humidity (RH) $\approx$98% (misting at 1-min intervals). The other group was placed on a non-misted bench with RH $\approx$60 to 80%, and was watered every other day. The experiment was repeated twice. All plants were fertilized with a controlled-release fertilize [Nutricot-Type 100 (16N-4.4P-8.3K); Chisso-Asahi®, Fertilizer Co. Ltd., Tokyo, Japan). Greenhouse temperature was maintained at 22±3° C.

After six weeks plants from the mist bench were transferred to the non-misted bench, and survival was recorded six weeks later. The effects of different substrates and acclimatization conditions on plant growth and development were assessed by measuring the fresh weights of plants after four months.

The data from all experiments were subjected to analysis of variance and regression procedures (SAS Institute, *SAS/STAT guide for personal computers*. Vers. 6. SAS Inst., Cary, N.C. 1987).

Results

Figure 5:
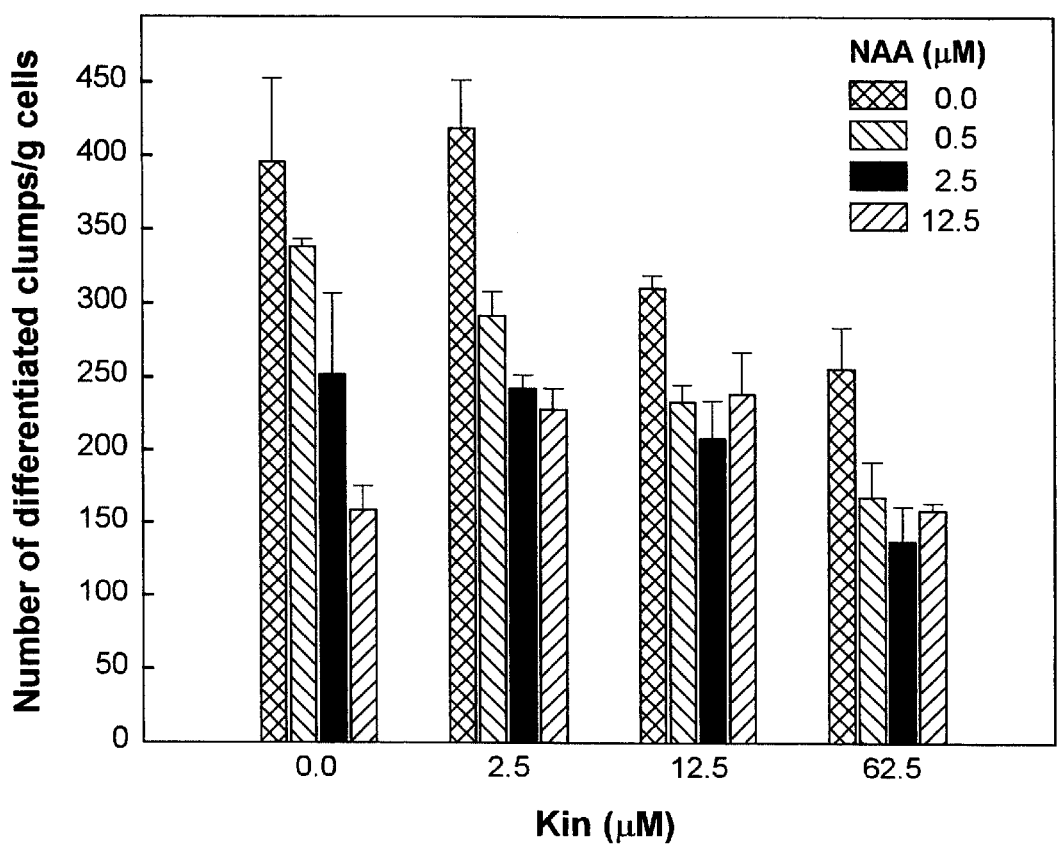
FIG. 5: Effects of Kin and NAA, alone and in combination, on the number of differentiated clumps from suspension-cultured cells of Iris germanica after six weeks on MS-I media. Vertical bars are standard errors.

Effects of kin and NAA, alone and in combination, in MS-I medium. Some white, globular embryo-like structures differentiated from suspension-cultured cells after two weeks on MS-I media. By Week 6, all 16 combinations of Kin and NAA had given rise to such structures, but the number of differentiated clumps differed significantly among growth regulator treatments (FIG. 5). ANOVA revealed that the main effects of Kin and NAA were significant ($P \leq 0.0001$), as well as the interaction effect ($P \leq 0.04$). The most differentiated clumps were obtained from the MS-I medium with 2.5 $\mu$M Kin and no NAA and from the MS-I medium without growth regulators. Generally, the lower concentrations of Kin and NAA induced the largest number of differentiated clumps per gram of suspension-cultured cells.

Six weeks after differentiated clumps were transferred to MS-D medium containing 1.25 $\mu$M BA, the clumps from MS-I media with 0.5 $\mu$M NAA and either 2.5 or 12.5 $\mu$M Kin showed the highest regeneration potential (67%; Table 3). The main effect of NAA, but not of Kin, on regeneration was significant ($P \leq 0.001$). However, most regenerating clumps developed plantlets (84 to 100%) irrespective of the NAA/Kin combinations.

The most desirable clumps (those larger than 10 mm) also were derived from the combination of 0.5 $\mu$M NAA and either 2.5 or 12.5 $\mu$M Kin.

TABLE 3

Effects of Kin and NAA, alone and in combination in MS-I medium, on subsequent regeneration potential of differentiated clumps of Iris tissue and development of shoots or plantlets (rooted shoots) after 6 weeks on MS-D medium with 1.25 $\mu$M BA.

| Growth regulator ($\mu$M) | No. of clumps tested | Regenerating clumps$^z$ (%) | Regenerating clumps developing (%): | |
|---|---|---|---|---|
| | | | SHOOTS ONLY | PLANTLETS |
| NAA | | | | |
| 0.0 | 41 | 23 | 12 | 89 |
| 0.5 | 43 | 56 | 6 | 94 |
| 2.5 | 36 | 55 | 11 | 89 |
| 12.5 | 38 | 33 | 7 | 94 |
| KIN | | | | |
| 0.0 | 43 | 37 | 7 | 93 |
| 2.5 | 45 | 41 | 5 | 96 |
| 12.5 | 36 | 44 | 12 | 89 |
| 62.5 | 36 | 45 | 12 | 88 |
| SIGNIFICANCE: | | | | |
| KIN | | NS | NS | NS |
| NAA | | *** | NS | NS |
| KIN × NAA | | NS | NS | NS |

$^z$Percentage of differentiated clumps that survived transfer from MS-I to MS-D media and developed shoots only or plantlets.
Symbol Key:
Non-significant ($^{NS}$) or significant (***) at $P \leq 0.001$, respectively.

Effect of BA concentration in MS-D medium. The concentration of BA did not have a significant effect on regeneration rate (%) but substantially influenced the development of large shoots from differentiated clumps (Table 4). The highest percentage of regenerating clumps (69%), i.e., differentiated clumps that survived transfer from MS-I to MS-D media and eventually developed shoots and plantlets, was obtained from MS-D medium containing 2.5 $\mu$M BA. However, only 55% of the differentiated clumps simultaneously developed both shoots and roots (plantlets) on this medium. The majority of shoots from the MS-D medium containing 2.5 $\mu$M BA showed poor rooting or developed no roots at all after transfer to MS-R medium. Apparently, this concentration of BA enhanced shoot development but inhibited rooting.

The MS-D medium containing 1.25 $\mu$M BA gave a slightly lower regeneration rate (67%) but strongly stimulated simultaneous development of shoots and roots (97%). Subsequently, shoots from the MS-D medium with 0 or 1.25 $\mu$M BA readily developed roots on the MS-R medium. In addition, the highest proportion of clumps (82%) that developed large shoots (>3 cm long) was obtained from the MS-D medium with 1.25 $\mu$M BA. Generally, the number of regenerated shoots ranged from 15 to 20 shoots/clump.

TABLE 4

Effect of BA concentration on development of shoots or plantlets (rooted shoots) from differentiated clumps$^z$ of Iris suspension cultures on MS-D medium.

| BA ($\mu$M) | No. of clumps tested | Regenerating clumps$^y$ (%) | Regenerating clumps developing (%): | | |
|---|---|---|---|---|---|
| | | | Shoots only | Plantlets | Large shoots$^x$ |
| 1.25 | 63 | 67 | 3 | 97 | 82 |
| 2.5 | 45 | 69 | 45 | 55 | 72 |
| $R^2$ | | 0.19$^{NS}$ | 0.08$^{NS}$ | 0.43$^{NS}$ | 0.59* |

$^z$The differentiated clumps were produced on MS-I medium containing 2.5 $\mu$M Kin and 0.5 $\mu$M NAA.
$^y$Percentage of differentiated clumps that survived transfer from MS-I to MS-D media and developed shoots only or plantlets.
$^x$Shoots > 3 cm long.
Symbol Key:
Non-significant ($^{NS}$) or significant (*) at $P \leq 0.05$.

Figure 6:
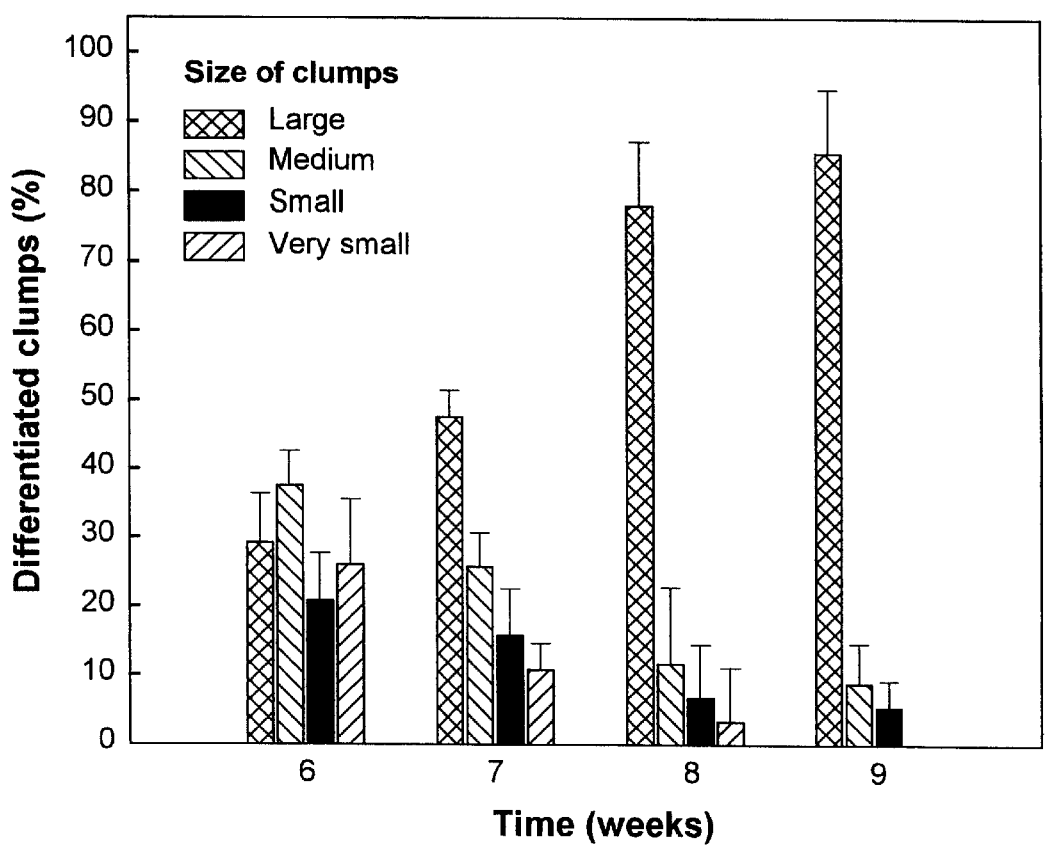
FIG. 6: Changes in distribution of clumps among four size classes during prolonged incubation (6 to 9 weeks) on MS-I medium containing 2.5 $\mu$M Kin and 0.5 $\mu$M NAA. Vertical bars are standard errors. Size classes are large (>10 mm), medium (5 to 10 mm), small (2 to 5 mm), very small (<2 mm).

Relationship between size and age of diffierentiated clumps and their regeneration potential. The changes in the distribution of clumps among the four size classes during prolonged incubation on MS-I media (with 2.5 $\mu$M Kin and 0.5 $\mu$M NAA) were monitored from Week 6 to Week 9. The proportion of large clumps (>10 mm) increased from 29% to 86% (FIG. 6). After six weeks on MS-I media, the regeneration potentials of the large, medium, small, and very small clumps were 100, 95, 91, and 82%, respectively (Table 5). During prolonged incubation on MS-I medium, regeneration of the large clumps remained high, while that of the medium, small and very small size clumps decreased sharply. Only 54, 35, and 0% of the medium, small and very small clumps, respectively, developed shoots after nine weeks of incubation. The ability to develop large shoots (>3 cm long) declined during prolonged incubation on MS-I medium, regardless of size (Table 5). The highest overall regeneration per gram of suspension-cultured cells was always obtained from six-week-old clumps.

The quality of regenerating clumps was also characterized by the size of shoots developing from different sized clumps after 6 weeks on MS-D medium containing 1.25 $\mu$M BA. The ability to develop large shoots (>3 cm long) declined with size of the clumps, as did the tendency to simultaneously develop both shoots and roots.

TABLE 5

Effects of age and size[z] of differentiated clumps of Iris suspension culture on regeneration potentials and development of large shoots[y].

| Age of clumps (weeks) | Regeneration (%) | | | | Clumps developing large shoots (%) | | | |
|---|---|---|---|---|---|---|---|---|
| | Large | Medium | Small | Very small | Large | Medium | Small | Very small |
| 7 | 100 | 93 | 85 | 63 | 91 | 66 | 38 | 17 |
| 8 | 100 | 73 | 56 | 39 | 78 | 55 | 26 | 10 |
| 9 | 98 | 54 | 35 | 0 | 74 | 37 | 23 | 0 |
| Significance: | | | | | | | | |
| AGE | | | *** | | | | *** | |
| SIZE | | | *** | | | | *** | |
| AGE × SIZE | | | *** | | | | NS | |

[z]Size classes: Large (>10 mm), medium (5 to 10 mm), small (2 to 5 mm), very small (<2 mm).
[y]Shoots > 3 cm long.
Symbol Key:
Non-significant ([NS]) or significant (***) at $P \leq 0.001$, respectively.

Effects of substrate type and acclimatization condition on plant establishment in the greenhouse. Plant survival and growth after transfer from in vitro culture to potting substrates under greenhouse conditions varied among eight different substrates ($P \leq 0.01$; Table 6). The substrates composed of peat moss, perlite and sandy loam or peat moss, pumice and sandy loam promoted the highest plant recovery and plant growth. The effect of misting on plant survival was not statistically significant (P>0.35).

TABLE 6

Effects of different potting substrates on plant survival and growth (fresh weight) of Iris plantlets after 6 months of cultivation in the greenhouse.

| Substrate | Survival (%) | Fresh weight (g) |
|---|---|---|
| Peat moss | 50 b[z] | 29 cd |
| Perlite | 58 b | 16 d |
| Sandy loam | 85 a | 48 bc |
| Peat moss:sandy loam | 70 ab | 55 ab |
| Peat moss:perlite | 85 a | 33 cd |
| Perlite:sandy loam | 88 a | 45 bc |
| Peat moss:perlite:sandy loam | 83 a | 71 a |
| Peat moss:pumice:sandy loam | 90 a | 68 a |

[z]Mean separation within columns by Duncan's multiple range test, $P \leq 0.05$.

The specific combination of auxin and cytokinin in culture media is one of most important factors for in vitro plant regeneration (Gozu et al., *Plant Cell Rpt.*, 13:12–16, 1993; Jéhan et al., *Plant Cell Rep.*, 13:671–675, 1994; Laublin et al., *Plant Cell Tiss. Org. Cult.*, 27:15–21, 1991; Radojević et al., *Acta Hort.*, 212:719–723, 1987; Radojević and Subotić, *J. Plant Physiol.*, 139:690–696, 1992; Shimizu et al., *Euphytica*, 89:223–227, 1996). Generally, 2,4-D is the most effective auxin for inducing embryogenic calli. However, 2,4-D in liquid medium is essential for suspension cultures to grow continuously, and stimulates formation of proembryogenic or proorganogenic masses.

Kinetin has been used extensively in the induction and maintenance of embryogenic callus in Iris (Gozu, et al., *Plant Cell Rpt.*, 13:12–16, 1993; Jéhan, et al., *Plant Cell Rep.*, 13:671–675, 1994; Radojević and Subotić, *J. Plant Physiol.*, 139:690–696, 1992; Shimizu, et al., *Euphytica*, 89:223–227, 1996, Shimizu et al., *Plant Cell Tiss. Org. Cult.*, 50:27–31, 1997). Somatic embryogenesis and/or shoot organogenesis is induced when embryogenic calli are transferred to media containing low or no Kin. In the current study, lower concentration of Kin was more desirable for inducing plant morphogenesis (somatic embryogenesis and shoot organogenesis) from iris suspension-cultured cells.

Kawase et al. concluded that shoot regeneration from perianth-ovary junctions and ovaries of Japanese iris (*Iris ensata* Thunb.) was strongly affected by BA and NAA in the medium (*J. Jpn. Soc. Hort. Sci.*, 64: 143–148, 1995). They found that high concentrations of both BA and NAA inhibited rooting of the upper portions of ovary explants. The herein-disclosed research demonstrates that the BA concentration did not have a significant effect on percentage regeneration but substantially influenced the development of shoots and plantlets from differentiated clumps. For example, while the MS-D medium with 2.5 μM BA enhanced shoot development, only 55% of regenerating clumps from this medium simultaneously developed shoots and roots (plantlets) (Table 4). Furthermore, 2.5 μM BA in the MS-D medium inhibited subsequent rooting on MS-R medium. Although a concentration of 1.25 μM gave somewhat lower regeneration rates (67%), it strongly promoted development of plantlets (97%; Table 4). Shoots from this medium readily rooted after transfer to an MS-R medium.

Based on the results reported in Examples 1 and 2, optimal conditions for efficient in vitro plant regeneration from suspension-cultured cells of Iris include the following:

1) suspension-cultured cells should be grown in MS-L medium containing 5 μM 2,4-D and 0.5 μM Kin in the dark at 25° C. for 6 weeks;
2) the cells should be passed through a 30-mesh stainless sieve to select cell clusters with diameter ≦520 μm;
3) the screened cells should be inoculated onto MS-I medium containing 2.5 to 12.5 μM Kin and 0.0 to 0.5 μM NAA, then cultured in the dark at 25° C. for six weeks;
4) the differentiated clumps should be transferred to MS-D medium containing 1.25 μM BA and incubated under light (50 μmol m$^{-2}$ s$^{-1}$) at 23° C. for 6 weeks;
5) well-developed shoots and plantlets should be transferred to MS-R medium for root initiation and development; and
6) the rooted plantlets should then be transplanted to the greenhouse in a substrate containing peat moss, pumice, sandy loam (1:1:1, v/v/v).

Under these conditions, about 8000 plantlets [≈400 differentiated clumps/g cells×15 to 20 shoots/clump] can be regenerated from 1 gram of iris suspension-cultured cells in about four months. The efficiency of this regeneration protocol is about four times as high as that reported by Shimizu et al. (*Plant Cell Tiss. Org. Cult.*, 50:27–31, 1997).

Example 3

Genetic Transformation of *Iris Germanica* Mediated by *Agrobacterium Tumefaciens*

Overview

A protocol was developed for production of transgenic iris plants (*Iris germanica* L. 'Skating Party') from regenerable suspension cultures via Agrobacterium-mediated transformation. A series of selection agents were tested, and hygromycin and geneticin were identified as particularly suitable for selecting transformed iris cells. Suspension cultures of iris were co-cultured for three days with *Agrobacterium tumefaciens* LBA 4404(pTOK233) carrying an intron-interrupted uidA (GUS) gene encoding β-glucuronidase, and hpt (hygromycin) and nptII (geneticin) selectable marker genes. Hygromycin- or geneticin-resistant calli having GUS enzyme activity were identified and used to induce plant regeneration. Over 300 morphologically normal transgenic iris plants were obtained in about six months. About 80% of the transformants were GUS-positive and NPTII-positive (paromomycin-resistant). Integration of transgenes into the nuclear genome of iris plants was confirmed by Southern blot analysis. This method is an efficient *A. tumefaciens*-mediated transformation system for *Iris germanica L.*, which enables modification and improvement of this horticulturally important ornamental monocot via genetic engineering.

Materials and Methods

Suspension cultures. Cell suspension cultures of *Iris germanica* 'Skating Party', capable of plant regeneration, were established using the methods described in Examples 1 and 2. Cultures were maintained in MS-L medium [MS basal medium (Murashige and Skoog, *Physiol. Plant.*, 15:473–497, 1962), containing 50 g·L$^{-1}$ sucrose, 290 mg·L$^{-1}$ proline, 0.5 µM kinetin (Kin), and 5.0 µM 2,4-dichlorophenoxyacetic acid (2,4-D) pH 5.9 in the dark at 25° C. on a gyratory shaker (120 rpm), and were subcultured every three to four weeks.

Evaluation of selection agents. There is no information available on agents that are suitable for selection of stable iris transformants. To determine the efficacy of several commonly used agents for selecting transformed iris cells, the following substances were tested: five antibiotics (methotrexate, hygromycin, geneticin (G418), gentamycin, and phleomycin); three herbicides (glyphosate [N-(Phosphonomethyl)glycine] (Monsanto, St. Louis, Mo.), chlorsulfuron [2-Chloro-N-[[(methoxy-6-methyl-1,3,5-triazin-2-yl)amino]carbonyl]benzenesulfonamide] (E.I. Du Pont de Nemours & Co., Inc., Agricultural Products Dept., Wilmington, Del.) and glufosinate-ammonium (Basta; Hoechst Canada, Inc., Regina, Saskatchewan, Canada)); and one amino acid analog (4-methyl-tryptophan) (Sigma). These agents were chosen because genes conferring resistance to those compounds have been cloned (reviewed by Schrott (*Selectable markers and reporter genes*, p. 325–336. In: Potrykus and Spangenberg (eds.). *Gene transfer to plants*. Springer-Verlag Berlin, 1995). The efficacy of each selection agent was evaluated by its ability to suppress growth of non-transformed iris cells on medium containing increasing levels of the selection agent.

The liquid MS-L medium was removed from a three-week-old iris suspension culture and the cells spread on Whatman No. 1 filter papers (42.5 mm diameter) in small culture plates (60 mm×15 mm), over MS-C medium [MS-L medium with 3 g·L$^{-1}$ Phytagel (Sigma Chem. Co., St. Louis, Mo.), as described in Examples 1 and 2] containing increasing amounts of the selection agent. Plates were incubated for three weeks in the dark at 25° C. In preliminary experiments, five concentrations of each selection agent were tested and inhibition of cell growth was scored visually. Among the nine compounds tested, 4-methyl-tryptophane, gentamycin, phleomycin, and glyphosate did not clearly inhibit growth, and were excluded from further testing.

The five most effective selection agents from preliminary experiments were re-assayed. Fresh weights of resultant tissue were measured and mean values, expressed as a percentage of growth by controls (no selection agent). At least five plates were used for each concentration of selection agent.

Bacterial strain and plasmid vector. In preliminary studies, three *A. tumefaciens* strains [LBA 4404 (pTOK233), LBA4404 (pCAMBIA1201) and EHA105 (pCAMBIA1201)] were tested to identify the one giving the highest transient transformation rates. The *A. tumefaciens* strain LBA4404, harboring the super-binary vector, pTOK233, was obtained from Japan Tobacco, Inc., Shizuoka, Japan (Hiei et al., *Plant J.*, 6:271–282, 1994). The pCAMBIA1201 binary vector (CAMBIA, Canberra City, Australia) was transformed into *A. tumefaciens* LBA4404 (Hoekema et al., *Nature*, 303:179–180, 1983) and EHA105 (Hood et al., *Transgenic Res.*, 2:208–218, 1993) according to the procedure described by Walkerpeach and Velten (B1, p. 1–19. In: Gelvin and Schilperoort (eds.), *Plant molecular biology manual*, Kluwer Academic Publishers, Dordrecht, The Netherlands, 1994). All strains contained a hygromycin resistance gene (PCaMV35S-hpt-T35S) and an intron-interrupted GUS (PCaMV35S-uidA-TNOS) gene within the T-DNA borders. pTOK233 also contained a geneticin resistance gene (PNOS-nptII-TNOS). They were grown on solid AB medium (Chilton et al., *Proc. Natl. Acad. Sci. USA*, 71:3672–3676, 1974), containing appropriate antibiotics, at 28° C. for three days. The bacteria were harvested and resuspended in AAM medium (Hiei et al., *Plant*, 6:271–282, 1994) to give an absorbance of 1.8 at 600 nm.

Transformation. Three-week-old iris suspension cultures grown in MS-L medium were used for transformation experiments. The MS-L medium was removed from the culture and *A. tumefaciens* suspension (25 mL) was added. The flask was gently shaken, and left to stand for five minutes. The liquid phase was removed and cells were spread onto MS-C-AS medium (MS-C medium with 10 g·L$^{-1}$ glucose, 100 µM acetosyringone; pH 5.2), then incubated in the dark at 25° C. for three days.

Selection of transformants. After three days co-cultivation, the cells were collected with a spatula and rinsed thoroughly with 250 mg·L$^{-1}$ cefotaxime (Claforan; Hoechet-Roussel Pharmaceuticals, Inc., Somerville, N.J.) dissolved in sterile water. Half the washed cells were spread on MS-C medium containing 250 mg·L$^{-1}$ cefotaxime and 50 mg·L$^{-1}$ hygromycin, the other half on MS-C medium containing 250 mg·L$^{-1}$ cefotaxime and 50 mg·L$^{-1}$ G418. The cells were then cultured in the dark at 25° C. for three weeks. Cell clumps that proliferated on these selection media were transferred to the second selection media (MS-C containing 250 mg·L$^{-1}$ cefotaxime and either 100 mg·L$^{-1}$ hygromycin or 100 mg·L$^{-1}$ G418) and cultured for another three weeks under the same conditions.

Cell clumps that continued to grow on the second selection media were assayed for expression of the GUS gene as described below. Only those clumps that tested GUS-positive were transferred individually to small culture plates containing 10 mL MS-I media (Table 1) containing 250 mg·L$^{-1}$ cefotaxime and either 50 mg·L$^{-1}$ hygromycin (MS-I-H) or 50 mg·L$^{-1}$ G418 (MS-I-G), to induce plant regeneration. They were cultured in the dark at 25° C. for three weeks. Cell clumps displaying typical morphogenic changes were selected and transferred to MS-D medium (Table 1) containing 250 mg·L$^{-1}$ cefotaxime and either 50 mg·L$^{-1}$ hygromycin or 50 mg·L$^{-1}$ G418, in Magenta GA-7 vessels (Sigma) and cultured for two-three weeks at 23° C. with a 16 hour photoperiod of 50 µmol·m$^{-2}$ s$^{-1}$ provided by cool-white fluorescent lamps. Irradiance was measured on the top of Magenta GA-7 vessel with a Quantum/Radiometer/Photometer (LI-189; Li-Cor, Inc., Lincoln, Nebr.).

Shoots and plantlets (rooted shoots) were transferred to MS-D medium without selection agents to facilitate growth and development for another two-three weeks. Both shoots and plantlets were then transferred to MS-R medium (Table 1) in Magenta GA-7 vessels for root induction and development. They were subcultured every other week on this medium.

Well-rooted plantlets (4–6 cm shoot length) were transferred to a growing medium containing 3 peat: 2 pumice: 1 sandy loam (v/v/v) in 250-mL pots and acclimatized on a mist bench (relative humidity=95–98%) in a greenhouse maintained at 16 hour days/8 hour nights of 25±3/20±3° C. Light was supplemented by high-pressure sodium lamps (Energy Technics, York, Pa.) providing photosynthetically active radiation (PAR) of 400–500 $\mu mol \cdot m^{-2} \cdot s^{-1}$ at the surface of growing medium. Four to five weeks later the plants were moved to a non-misted bench and fertilized with controlled-release fertilizer Nutricot-Type 100 (16N-4.4P-8.3K; Chisso-Asahi®, Fertilizer Co., Ltd., Tokyo, Japan).

Assay for gus activity. To determine transient transformation rates, a few cells were collected with a spatula three days after co-cultivation with *A. tumefaciens*, and washed thoroughly with a 0.1 M sodium-phosphate buffer (pH 7.2) to remove surface bacteria. Cells were spread on filter paper in a small culture plate and 1 mL of the GUS-staining solution [0.1 M sodium phosphate buffer pH 7.2, 5 mM $K_3[Fe(CN)_6]$, 5 mM $K_4[Fe(CN)_6]$, 10 mM EDTA, 20% methanol (v/v), 0.01% Triton X-100 (v/v), and 1 $mg \cdot mL^{-1}$ 5-bromo-4-chloro-3-indolyl glucuronide] was added. Each plate was then sealed with Parafilm and incubated overnight at 37° C.

To identify GUS-positive cell clumps from the second selection media, a small piece (3–4 mm diameter) of each clump was placed on filter paper in small culture plates. One milliliter of staining solution was added to each plate; then the plates were sealed with Parafilm and incubated at 37° C. overnight.

Regenerated structures (globular embryo-like structures and shoot primordia) were excised and stained for GUS activity in 100 $\mu L$ staining solution in microcentrifuge tubes. The samples were infiltrated with staining solution under vacuum for about 10 minutes and incubated overnight at 37° C.

Slices of green leaves (2-mm) and roots (5-mm) were placed in microcentrifuge tubes with 100 $\mu L$ of staining solution. They were infiltrated with staining solution under vacuum for 10 minutes and stained overnight at 37° C. Chlorophyll from green leaves was bleached out with several changes of 95% ethanol before results were scored.

Functional assay of NPTII genes. To test the NPTII expression in transformed iris plants, the leaf-bleach assay was carried out according to Cheng et al. (*Plant Physiol.*, 115:971–980, 1997), with minor modifications described below. Four pieces (≈7-mm) were cut from the second youngest leaf of each plant approximately one month after establishment in growing medium in the greenhouse. One leaf piece was placed in 1 mL of solution containing 25 $mg \cdot L^{-1}$ benomyl fungicide [methyl 1-(butylcarbamoyl)-2 benzimidazolecarbamate] (Hi-Yield Chem. Co., Bonham, Tex.) and 0.01% Triton X-100 (Sigma), in a well of 24-well culture plate, as a control. Each of the remaining three pieces were placed in 1 mL of the same solution with either 50, 100, or 200 $mg \cdot L^{-1}$ paromomycin (Sigma). Leaf samples from the non-transformed iris plants at a similar developmental stage were used as a negative control. The samples were vacuum-infiltrated for 10 minutes. The plates were then sealed with Parafilm and incubated for five days at 23° C. with a 16 hours photoperiod of 50 $\mu mol \cdot m^{-2} \cdot s^{-1}$ provided by cool-white fluorescent lamps. In preliminary assays, G418 and hygromycin were also tested, the latter for the functional expression of the hpt gene. The response to all three antibiotics was very similar, so paromomycin was selected to assay the rest of the putative transgenic iris plants because it was least expensive.

DNA isolation and southern hybridization analysis. DNA was extracted from four grams of young leaves using the protocol of Rawson et al. (*Biochem. Genet.*, 20:209–219, 1982) as modified by Davis et al. (*J. Hered.* 89:319–323, 1998). The leaf tissue was homogenized in 40 mL grinding buffer (100 mM Tris, 25 mM EDTA, 0.35 M sucrose, 50 mM KCl, 5% polyvinylpyrrolidone, 10 mM diethyldithiocarbamic acid, and 0.2% mercaptoethanol), using a Waring 250-mL stainless steel blender for 15 seconds. The homogenate was filtered through cheesecloth and centrifuged at 12,000 $g_n$ for 20 minutes at 4° C.

The pellet was resuspended in 6 mL lysis buffer (100 mM EDTA; 50 mM Tris-HCl, pH 8.0; 2.5% Triton X-100; 2% sarkosyl; 50 $\mu g \cdot mL^{-1}$ Proteinase K) and incubated at 37° C. in a shaking incubator for 2 hours. The lysate was then centrifuged at 15,000 $g_n$ for 10 minutes (4° C.), and the supernatant was precipitated with 2/3 volume isopropanol at −20° C. for 30 minutes. The precipitate was pelleted at 20,000 $g_n$ for 15 minutes at 4° C. Afterward, the pellet was resuspended in TE buffer (10 mM Tris-HCl, 1 mM EDTA; pH 8.0) and the DNA was purified further through a CsCl gradient as described by Rawson et al. (*Biochem. Genet.*, 20:209–219, 1982). The DNA sample was precipitated, washed with 70% ethanol, and resuspended in TE buffer at a concentration of 1 $\mu g \cdot L^{-1}$.

Southern blot analysis was performed as described by Sambrook et al. (*Molecular cloning: A laboratory manual*. 2nd, Cold Spring Harbor Laboratory Press. Plainview, N.Y., 1989). Briefly, the method involved digesting 20 $\mu g$ genomic DNA with HindIII, resolving the digested material on a 0.8% agarose gel, then blotting onto a nylon membrane (Zetaprobe, Bio-Rad, Richmond, Calif.). Identically prepared blots were probed with radiolabeled GUS or hpt DNA fragments. A 250 bp fragment in the GUS coding region and a 608 bp fragment in the hpt coding region were PCR-amplified according to Gould et al. (*Plant Physiol.*, 95:426–434, 1991) and Abedinia et al. (*J. Plant. Physiol.*, 24:133–141, 1997), respectively for use as hybridization probes. PCR-amplified fragments were labeled with [$^{32}P$] dCTP by random priming (Feinber and Vogelstein, *Anal. Biochem.*, 123:6–13, 1983) and used as probes. The blots were first washed at low stringency (2×SSC, 0.1% SDS) twice at 65° C. (30 minutes each) followed by two washes (30 minutes each) at moderate stringency (0.5×SSC, 0.1% SDS) at 65° C. Blots were autoradiographed with an intensifying screen at −85° C. for five days.

Results

Figure 7:
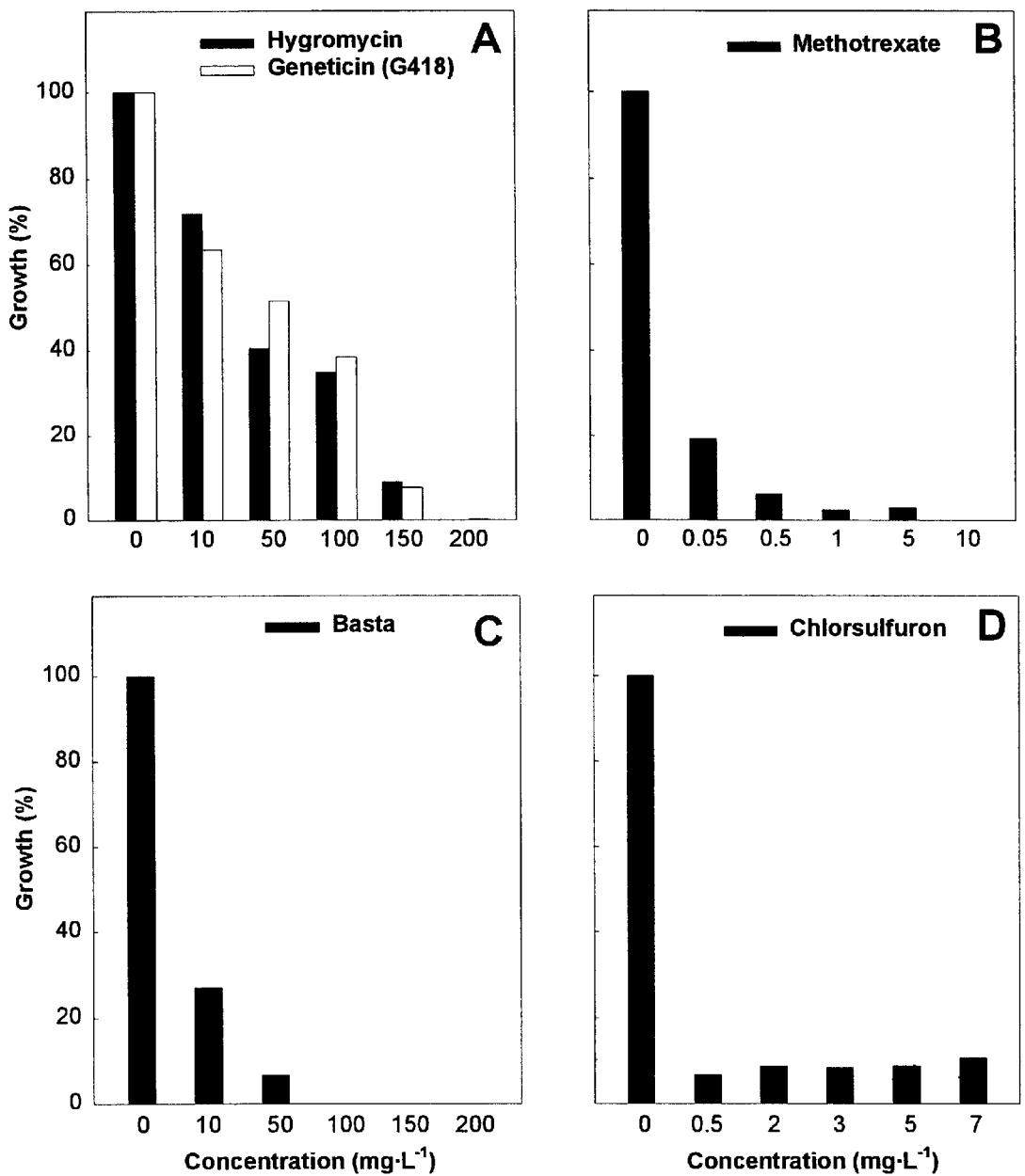
FIG. 7: Effect of three antibiotics [(A) hygromycin and geneticin (G418), and (B) methotrexate] and two herbicides [(C) Basta and (D) chlorsulfuron) on growth of non-transformed iris suspension-cultured cells. Each data point represents at least five replicates.
Figure 8:
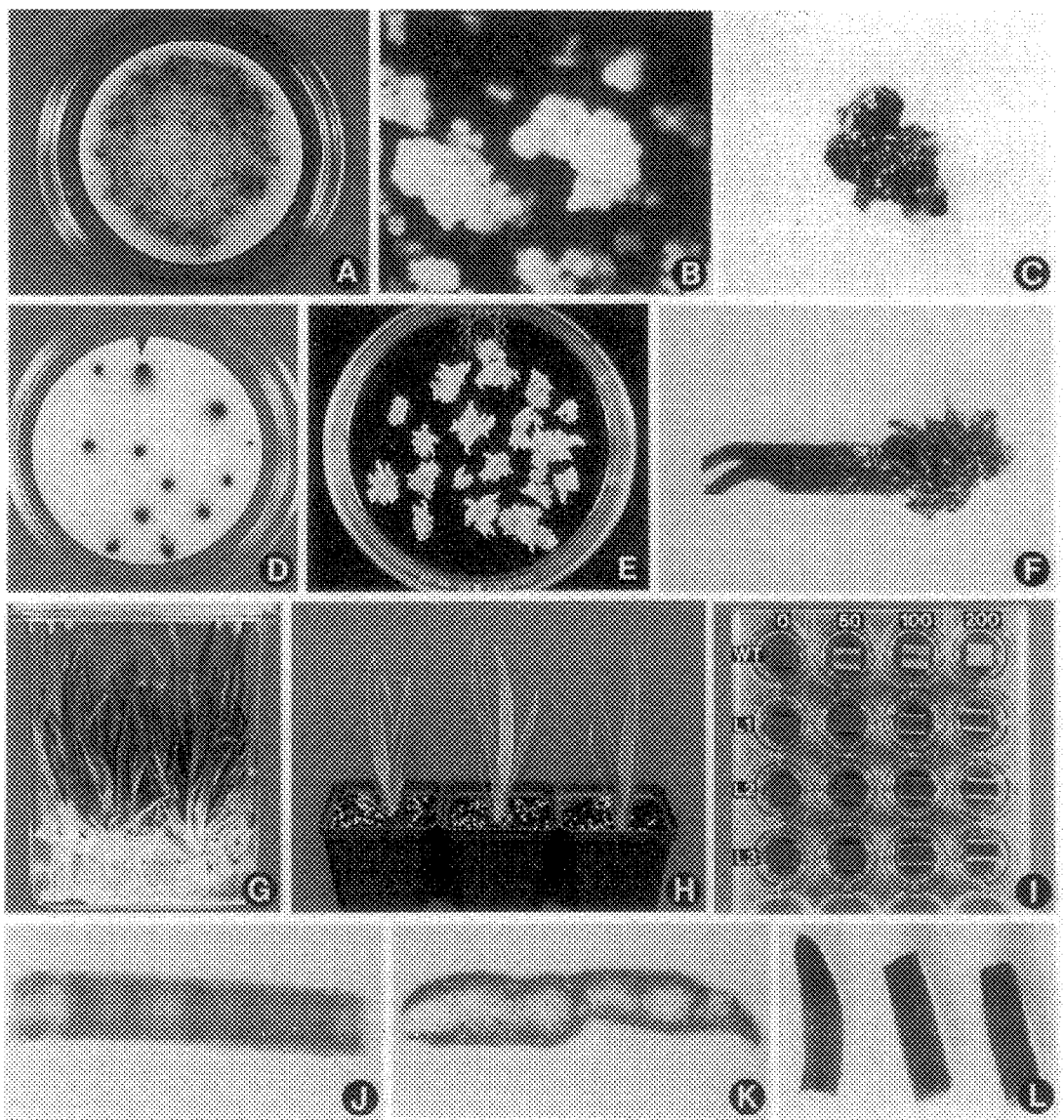
FIG. 8: Transient expression of the GUS gene in A. tumefaciens-infected suspension-cultured iris cells, stable GUS expression in various tissues from transgenic plants, and steps in the regeneration of transgenic plants.

Evaluation of selection agents. Increasing the concentration of hygromycin and geneticin (G418) resulted in a gradual decrease in the percentage of iris cell growth. Hygromycin and geneticin were used separately for transformation experiments because pTOK233 contains both hpt and nptII selectable marker genes for plant cells, rendering them resistant to either hygromycin or geneticin. Both hygromycin and geneticin at concentrations of 50 to 100 $mg \cdot L^{-1}$ caused 40%–50% growth inhibition (FIG. 7). A two-step-selection was employed, first 50 $mg \cdot L^{-1}$ and then 100 $mg \cdot L^{-1}$ for both selection agents. The two-step selection (3+3 weeks) allowed recovery of a large enough mass of each independent callus line for efficient induction of multiple shoots in subsequent regeneration experiments. Higher concentrations of either antibiotic were not used because there was the possibility of inhibiting plant regeneration from transgenic callus tissue.

Cell growth, however, was greatly inhibited at 0.05 $mg \cdot L^{-1}$ methotrexate (≈80%), 10 $mg \cdot L^{-1}$ Basta (≈70%), and 0.5 mg·L$^{-1}$ chlorsulfuron (≈90%) (FIG. 7B, 7C, and 7D). In a preliminary study on the use of microparticle bombardment for iris transformation, transgenic calli selected on 10 mg·L$^{-1}$ Basta showed very low regeneration potential.

Transformation and regeneration of transgenic iris plants. Agrobacterium strain LBA4404 (pTOK233) gave remarkably higher transient transformation rates than either LBA4404 (pCAMBIA1201) or EHA105 (PCAMBIA1201), and was therefore used for the stable transformation experiments. EHA105 (pCAMBIA1201) gave higher transient transformation rates than LBA4404 (pCAMBIA1201). The plasmid pTOK233 belongs to a class called "super-binary vectors," because it carries the virB, virC, and virG genes of A281, a highly efficient strain for transforming higher plants (Komari, *Plant Cell Rpt.*, 9:303–306, 1990). Introduction of a DNA fragment from the virulence region of Ti-plasmid into a binary vector or into a separate plasmid has been shown to lead to the increased virulence of *A. tumefaciens* and much higher transformation rates in several plant species (Arias-Garzón and Sarria, *Proc. Second Intl. Scientific Mtg. of The Cassava Biotechnol. Network*, CIAT Working Document 150, 1:245–251, 1995; Hiei et al., *Plant J.*, 6:271–282, 1994; Li et al., *Nature Biotechnol.*, 14:736–740, 1996; Liu et al., *Plant Mol. Biol.*, 20:1071–1087, 1992; Wenck et al., *Plant Mol. Biol.*, 39:407–416, 1999).

After three days co-cultivation on MS-C-AS medium with *A. tumefaciens*, the infected cells three were transferred to the first two selection media (MS-C containing 250 mg·L$^{-1}$ cefotaxime and either 50 mg·L$^{-1}$ hygromycin or 50 mg·L$^{-1}$ G418). At that time a sample of cells was stained for expression of the GUS gene. Many cells and small cell aggregates stained dark blue, confirming that T-DNA transfer occurred. GUS expression most likely occurred in the transformed cells and not in pTOK233-containing Agrobacterium because the presence of an intron in the GUS coding region efficiently prevented its expression in bacterial cells (Ohta et al., *Plant Cell Physiol.*, 31:805–813, 1990). After ten days, several of the cell clumps that proliferated on the first selection media were stained for GUS activity. Most clumps were stained uniformly dark blue, but some clumps also contained unstained patches.

After three weeks on the first two selection media, about 300 independent clumps were selected from each medium and transferred to the second two selection media, which contained an increased concentration of selection agents. Most calli transferred to a medium containing G418 continued to grow much more slowly than those transferred to a medium containing hygromycin. The slower growth of transformed callus tissue on G418-containing media may be due, at least in part, to the difference in promoter strength. In pTOK233, the hpt and nptII genes are driven by CaMV35S and NOS promoters, respectively. In preliminary experiments using microprojectile bombardment, it was found that transient expression of PCaMV35S-uidA-TNOS was much higher than that of PNOS-uidA-TNOS.

Independent callus lines obtained through the two-step selection (175-hygromycin resistant, 50-G418 resistant) were then assayed for expression of GUS. About 61% of hygromycin-resistant and 46% of the G418-resistant callus lines tested GUS-positive. After overnight incubation in the GUS-staining solution, most of the GUS-positive cell clumps were stained dark blue, indicating very strong expression of the GUS gene (FIG. 2D). All callus lines that tested GUS-negative were discarded; only GUS-positive lines were transferred to MS-I media to induce plant regeneration. A total of 98 hygromycin-resistant, GUS-positive callus lines were transferred to MS-I medium containing 250 mg·L$^{-1}$ cefotaxime and 50 mg·L$^{-1}$ hygromycin. Twenty-two G418-resistant, GUS-positive callus lines were transferred to MS-I medium containing 250 mg·L$^{-1}$ cefotaxime and 50 mg·L$^{-1}$ G418. Some globular embryo-like structures appeared in about one week. After three weeks, 50 hygromycin-resistant and ten G418-resistant, GUS-positive, independent transgenic callus lines had developed numerous shoot primordia. Upon histochemical assay for expression of the GUS gene, ≈80% stained dark blue indicating that GUS activity was not affected by shoot morphogenesis.

Green shoots and plantlets (10–20 from each transgenic line) that developed on MS-D media were transferred to MS-R medium to induce and facilitate root development. More than 90% of the shoots rooted readily and were transferred eventually to growing medium. Eighty to 90% of plants survived transfer to the greenhouse and developed into morphologically normal plants.

Analyses of transgenic plants. Putative transgenic plants were assayed for expression of the GUS and NPTII genes. A total of 92 plants from 36 independent lines were assayed for GUS activity. About 80% of those plants were GUS-positive (Table 8). Expression of the GUS gene was very strong in both leaves and roots, as judged by the intensity of staining in those tissues).

Expression of the NPTII gene was assessed by a leaf-bleach assay in 60 transgenic plants from 33 independent lines. About 85% of those plants were resistant to paromomycin (NPTII$^+$) (Table 8). Leaf samples from resistant transgenic plants remained green, except on the cut edges at higher paromomycin concentrations. The leaf samples from control (non-transgenic) plants, however, were almost completely bleached at 200 mg·L$^{-1}$ paromomycin.

A total of 58 plants from 26 independent lines were assayed for co-expression of the GUS and NPTII genes. Seventy-eight percent of them co-expressed both genes (Table 8, Parts I and II).

TABLE 8

Expression of the GUS and NPTII genes in hygromycin (Hyg) and geneticin (G418) resistant Iris plants as determined by the histochemical staining and the leaf-bleach assay, respectively.

Part I

| Selection agent | No. plants (lines) assayed | GUS$^+$ | GUS– | No. Plants (lines) assayed | NPTII$^+$ | NPTII– |
|---|---|---|---|---|---|---|
| Hyg | 73 (30) | 61 | 11 | 51 (27) | 45 | 6 |
| G418 | 20 (6) | 13 | 7 | 9 (6) | 6 | 3 |
| Total | 92 (36) | 74 | 18 | 60 (33) | 51 | 9 |
| Percent | | 80 | 20 | | 85 | 15 |

Part II

Co-expression of GUS AND NPTII

| Selection agent | No. plants (lines) assayed | GUS$^+$ NPTII$^+$ | GUS$^+$ NPTII– | GUS– NPTII$^+$ | GUS– NPTII– |
|---|---|---|---|---|---|
| Hyg | 50 (23) | 40 | 1 | 4 | 5 |
| G418 | 8 (3) | 5 | 0 | 0 | 3 |
| Total | 58 (26) | 45 | 1 | 4 | 8 |
| Percent | | 78 | 2 | 7 | 14 |

To demonstrate stable transformation of iris plants with the hpt and GUS genes, four independent transgenic plants were subjected to Southern blot analysis. In pTOK233, the hpt gene is located next to the left border of the T-DNA region. The first HindIII site inside the T-DNA from the left border cuts at the 3'-end of the of the hpt cassette. Digestion of genomic DNA with HindIII, and subsequent hybridization with the hpt probe for the coding sequence identifies border fragments between the integrated T-DNA and plant DNA, thus giving rise to different fragment lengths, depending on location of insertion in the genome. HindIII also cleaves the entire GUS coding region from the T-DNA as a 3.1 kb fragment. DNA blot analysis of HindIII-digested genomic DNA from our GUS-positive/hygromycin-resistant plants, using the GUS probe, identified several banding patterns. Some of the samples indicate the presence of a truncated GUS insert (i.e., inserted GUS cassette slightly smaller than expected). Additional bands with larger sizes may be due to incomplete digestion of genomic DNA or possibly deletion of the flanking HindIII site(s). Despite the GUS gene size polymorphisms, β-glucuronidase activity was readily detectable. The GUS probe did not hybridize to any DNA from non-transformed plants.

Stable integration of the hpt gene into the iris genome was detected by a $^{32}$p-labeled DNA fragment from the coding region of the hpt gene. Both single and multiple hpt copy insertion(s) into different loci of the iris nuclear genome were found. Some inserted hpt fragments were smaller than the minimum expected size (4.8 kb). Those smaller sized bands may be due to rearrangement in the integrated genes but none of the tested plants showed loss of tolerance to hygromycin. No hpt sequence was detected in the non-transformed sample.

Using the methods described herein, over 300 putative transgenic plants were obtained in about six months. About 80% of tested plants were deemed transgenic based on GUS-positive staining and their antibiotic-resistant phenotype. The Southern blot data confirmed stable integration of the transgenes into the iris genome. GUS-positive and paromomycin-resistant phenotypes of those plants are indicative of the functional transgene expression. The CaMV35S promoter seems to be a strong promoter for iris plants, as indicated by the intensive color development during GUS staining. Thus, this promoter should be a good choice for the expression of gene(s) of interest in iris plants.

This work demonstrates that Agrobacterium-mediated transformation can be applied to horticulturally important monocotyledonous ornamentals, such as Iris. The newly developed Agrobacterium-mediated transformation method can be used to complement conventional breeding for improvement of Iris. Transferring genes from heterologous species provides a means of introducing new traits into the Iris genome, thus expanding the gene pool beyond what has been available in traditional iris breeding systems.

Example 4

Transformation of Iris Germanica Using Microparticle Bombardment

Media used for tissue culture and microparticle bombardment transformation of Iris are given in Table 1. Establishment and maintenance of suspension cultures. Newly sprouted shoots (≈40 to 50 mm tall) were excised from the stock plants and used for callus induction. Two to three of the outermost leaves are removed from each shoot. The basal portions were excised and washed thoroughly with tap water, immersed in 75% ethanol for one minute, then in 1% sodium hypochlorite containing Tween 20 (2 to 3 drops/100 mL). They were gently shaken on a rotary shaker (100 rpm) for 25 minutes, and then rinsed three times with sterile water. The basal portion of each leaf was carefully separated from the shoot and sliced into approximately 5-mm-thick pieces. The explants were placed on MS-C medium (Table 1) to induce callus development. Calli were cultured in the dark at 25° C. and subcultured every three weeks on the same type of medium.

To establish suspension culture, about 1 gram of callus tissue was transferred to a 250-mL Erlenmeyer flask containing 75 mL of MS-L medium (Table 1), incubated in the dark at 23° C. on a rotary shaker at 100 rpm, and subcultured monthly. If suspension cultures were to be maintained for an extended period of time they were screened through stainless steel sieve (30 mesh) to get rid of big clumps, which show low regeneration potential.

Transformation method using microprojectile bombardment. Three-to four-week-old iris suspension culture was screened through stainless steel sieve (30 mesh) and the pass-through fraction was used form transformation. Cells were pretreated in MS-L medium supplemented with 0.4 M osmoticum (an equimolar concentration of sorbitol and mannitol) for two hours with gentle shaking on a gyrator shaker (≈120 rpm). Pretreated cells were allowed to settle by gravity, or were centrifuged at 2500 rpm for 10 minutes, and the liquid medium was discarded. Pretreated cells were then spread onto a filter paper disk placed on MS-C medium containing 0.4 M osmoticum. Any of the devices used for biolistic transformation could be employed to deliver DNA-coated microparticles into pretreated cells. By way of example only, optimized parameters for PDS-1000 gene gun (Bio-Rad, Hercules, Calif.) were as follows:

| | |
|---|---|
| Tungsten particles | M-17 |
| Target distance | 6 cm |
| Helium pressure (rupture disks) | 1100 psi |
| Chamber vacuum | 25 in. Hg |

For transformation of iris cells via the biolistic method, a plasmid vector (usually small, high-copy number plasmid such as pUC or pbluescript) containing a selection marker expression cassette (e.g., P35S-hpt-Tnos), a reporter gene expression cassette (e.g., P35S-uidA-Tnos) and a gene of interest flanked by a promoter and a terminator for expression in plant cells could be used. After biolistic bombardment, the cells were incubated for about 24 to about 48 hours in the dark at 25° C. The cells were then transferred to MS-C medium and cultured for five days without selection to allow the cells to recover.

After recovery, the cells were transferred to MS-C medium containing selection agent (antibiotic or herbicide, as appropriate for the DNA construct used) and incubated in the dark at 25° C. for three to four weeks. Suitable selection agents for selecting transformed iris cells include hygromycin and geneticin in concentrations between 50 and 100 mg·L$^{-1}$. Clumps of proliferating cells were then transferred to fresh medium containing increased amount of selection agent (100 mg·L$^{-1}$), and cultured for an additional three to four weeks. After six to eight weeks on selection medium, clumps of proliferating cells were individually picked and transferred to a shoot induction medium (MS-I) containing selection agent. Shoots ≈5–10 mm long (after ≈2–6 weeks) were transferred to a shoot elongation and development medium (MS-D) and incubated under light for two to four weeks at 23° C. with a 16 hour photoperiod of 50 μmol·m$^{-2}$·s$^{-1}$ provided by cool-white fluorescent lamps. After green leaves grow to about 2–3 cm in length, individual plantlets were separated and transferred to root induction and development medium (MS-R). Well-rooted plantlets (4–6 cm shoot length) were transferred to a growing medium 3 peat: 2 pumice: 1 sandy loam (v/v) in 250-mL pots and acclimatized on a mist bench (relative humidity+98–98%) in a greenhouse maintained at 16 hour days/8 hour nights of 25±3/20±3° C. with a 16 hour photoperiod. Light in the greenhouse was supplemented by high-pressure sodium lamps to provide photosynthetically active radiation (PAR) of ≈400–500 $\mu mol \cdot m^{-2} \cdot s^{-1}$ at the surface of growing medium. Four to five weeks later, the plants were moved to a non-misted bench and fertilized with a controlled-release fertilizer such as Nutricot-Type 100[(16N-4.4P-8.3K); Chisso-Asahi®, Fertilizer Co., Ltd., Tokyo, Japan).

Analyses of stable integration and functional expression of transgene(s) was carried out as described above for the *A. tumefaciens*-mediated transformation. FIG. 9 illustrates plant material at several of the steps in biolistic transformation and regeneration of transgenic Iris plants, as described above. FIG. 9A shows transient transformation, represented by GUS activity (dark staining) in the cultured cells measured 48 hours after transformation, increasing with increasing concentrations of osmoticum (equimolar concentration of mannitol and sorbitol). FIG. 9B shows several cell clumps that proliferated on selection medium (MS-C containing 10 mg Basta), about 2 weeks later.

Two stable transformation of callus lines, designated #54 and #51, were confirmed by GUS staining (dark staining in FIG. 9C) several weeks later. Regenerated #54 plants, grown on MS-R medium, are shown in FIG. 9D. These plants, derived from #54 transgenic line, were hardened off and transfer to soil about 4 weeks later (FIG. 9E). Staining of the leaf section from a transgenic plant, demonstrating expression of the GUS gene (dark staining) is shown in FIG. 9F.

In addition, fast and reliable conformation of stable (integrative) transformation was done by PCR amplification of the coding region of transgene(s). The presence of GUS-encoding nucleic acids in the transgenic plants was demonstrated by specific amplification of a 250 bp fragment from the coding region of uidA (GUS) gene (FIG. 9G). The fragment was amplified from genomic DNA of several independent transgenic plants using PCR, and separated by agarose electrophoresis. Each transgenic plant tested (lanes 2 through 7) contained the same size band as the control (lane 8), while a non-transformed control plant (lane 9) showed no such band.

This invention provides methods for transforming and/or regenerating monocot plants, particularly commercially important ornamental monocots such as *Iris germanica*, as well as culture media that facilitate these transformation procedures. It will be apparent that the precise details of these methods and the described media may be varied or modified without departing from the spirit of the described invention. We claim all such modifications and variations that fall within the scope and spirit of the claims below.

What is claimed is:

1. A method of transforming *Iris germanica* cells, comprising:

selecting a cluster of *Iris germanica* cells in suspension culture with a diameter ≦520 microns;

introducing a recombinant nucleic acid molecule into the *Iris germanica* cells using a transformation method, where the transformation method comprises:

incubating the *Iris germanica* cells in a suspension comprising an Agrobacterium that comprises the recombinant nucleic acid molecule, or bombarding the *Iris germanica* cells with a microparticle that comprises the nucleic acid molecule;

initiating callus formation from the *Iris germanica* cells; and selecting transformed cells.

2. The method of claim 1, further comprising regenerating transgenic *Iris germanica* plants from the transformed cells.

3. The method of claim 1, wherein the transformation method comprises incubating the *Iris germanica* cells in a suspension comprising an Agrobacterium that comprises the recombinant nucleic acid molecule.

4. The method of claim 3, further comprising:

co-cultivating *Iris germanica* suspension culture cells with Agrobacterium cells containing a recombinant vector.

5. The method of claim 1, fluffier comprising:

regenerating transformed shoots from the transformed *Iris germanica* cells; and inducing root formation from the transformed shoots.

6. The method of claim 4, wherein the recombinant vector comprises a transfer DNA region.

7. The method of claim 4, wherein the recombinant vector comprises at least one protein-encoding polynucleotide sequence.

8. The method of claim 7, wherein at least one protein-encoding polynucleotide sequence encodes a selectable marker gene and transformed plant cells are selected by initiating callus formation in or on a medium that inhibits non-transformed plant cell growth.

9. The method of claim 1, wherein the Agrobacterium is *A. tumefaciens*.

10. The method of claim 9, wherein the *A. tumefaciens* comprises a regular binary vector, a co-integrative vector, a super binary vector, or a combination thereof.

11. The method of claim 1, wherein the recombinant nucleic acid comprises a sequence encoding a protein.

12. The method of claim 11, wherein the protein is selected from the group consisting of: irone synthetic proteins, plant pigment synthetic proteins, pesticide resistance proteins, fragrance proteins, senescence-related proteins, herbicide resistance proteins, and disease resistance proteins.

13. A transformed *Iris germanica* cell produced by the method of claim 1.

14. A transgenic *Iris germanica* plant, or part thereof, comprising the transformed *Iris germanica* cell of claim 13.

15. An *Iris germanica* plant derived from an *Iris germanica* cell that has been transformed by the method of claim 1, wherein the recombinants nucleic acid sequence comprises a functional gene that imparts a phenotype not possessed by the cell.

16. A cut flower from an *Iris germanica* plant regenerated from the transformed cells produced by the method of claim 1.

17. A method for culturing *Iris germanica* cells and regenerating transformed *Iris germanica* plants, comprising:

growing *Iris germanica* cells in suspension culture;

isolating cell clusters of ≦520 μm;

inoculating the isolated clusters into medium supplemented with at least one growth factor;

transforming the suspension cultured *Iris germanica* cells prior to initiating differentiation;

selecting for transformed clusters;

growing the clusters to initiate differentiation;

isolating differentiated clumps;

placing the differentiated clumps on a shoot regenerating medium to regenerate shoots and/or plantlets;

transferring regenerated shoots and/or plantlets to a root regeneration medium for root initiation; and transplanting rooted shoots and/or plantlets to soil.

18. The method of claim 17, wherein the *Iris germanica* cells are transformed using co-cultivation with *A. tumefaciens*.

19. A method for culturing *Iris germanica* cells and regenerating transformed *Iris germanica* plants, comprising:

growing *Iris germanica* cells in suspension culture in MS-L medium supplemented with 5 µM 2,4-D, 0.5 µM Kin in the dark for six weeks at 25° C.;

isolating cell clusters of ≦520 µm;

inoculating the isolated clusters into MS-I medium supplemented with about 2.5 to about 12.5 µM Kin and 0.0 to about 0.5 µM NAA;

transforming the suspension cultured *Iris germanica* cells prior to initiating differentiation;

selecting for transformed clusters;

growing the clusters in the dark for six weeks at 25° C. to initiate differentiation;

isolating differentiated clumps;

placing the differentiated clumps on MS-I with 1.25 µM BA under 50 µm/m²s at 23° C. for six weeks to regenerate shoots and/or plantlets;

transferring regenerated shoots and/or plantlets to MS-R for root initiation; and transplanting rooted shoots and/or plantlets to soil in a greenhouse.

20. The method of claim 19, wherein the *Iris germanica* cells are transformed using co-cultivation with *A. tumefaciens*.

* * * * *

UNITED STATES PATENT AND TRADEMARK OFFICE
CERTIFICATE OF CORRECTION

PATENT NO. : 6,459,017 B1
DATED : October 1, 2002
INVENTOR(S) : Jeknic et al.

It is certified that error appears in the above-identified patent and that said Letters Patent is hereby corrected as shown below:

Column 2,
Line 64, "posses" should read -- possess --.

Column 4,
Line 62, "(B)Several" should read -- (B) Several --.

Column 6,
Line 62, "a48 hours" should read -- 48 hours --.

Column 7,
Line 61, ",.1990" should read -- , 1990 --.

Column 8,
Line 14, "optimizing Rax" should read -- optimizing --.
Line 39, "34" should read -- 3-4 --.

Column 11,
Line 11, "et al. The" should read -- et al., The --.
Line 16, "wuni" should read -- wunI --.
Line 19, "108 1997)" should read -- 108, 1997) --.
Line 23, "1304 1993" should read -- 1304, 1993 --.

Column 13,
Table 1, "$L^1$" should read -- $L^{-1}$ --.
Line 66, "2.4-D" should read -- 2, 4-D --.
Line 66, "kinetin" shoud read -- Kinetin --.

Column 14,
Line 49, "capability," should read -- capability. --.
Line 66, "stabs" should read -- tabs --.

Column 16,
Line 19, "kin" should read -- Kin --.
Line 31, "anci" should read -- and --.

Column 21,
Line 12, "kin" should read -- Kin --.

UNITED STATES PATENT AND TRADEMARK OFFICE
CERTIFICATE OF CORRECTION

PATENT NO. : 6,459,017 B1
DATED : October 1, 2002
INVENTOR(S) : Jeknic et al.

It is certified that error appears in the above-identified patent and that said Letters Patent is hereby corrected as shown below:

Column 22,
Line 46, "6to" should read -- 6 to --.

Column 23,
Line 48, *missing heading "Discussion"*.
Line 49, "one of most" should read -- one of the most --.
Line 65, "1996," should read -- 1996; --.

Column 25,
Lines 18-20, "[MS basal medium (Mursashige and Skoog, *Physiol. Plant.*, 15:473-497, 1962)" should read -- [MS basal medium (Mursashige and Skoog, *Physiol. Plant.*, 15:473-497, 1962)] --
Lines 40-43, "(reviewed by Schrott (*Selectable markers and reporter genes*, p. 325-336. In: Potrykus and Spangenberg (eds.). *Gene transfer to plants*. Springer-Verlag Berlin, 1995)." should read -- (reviewed by Schrott (*Selectable markers and reporter genes*, p. 325-336. In: Potrykus and Spangenberg (eds.). *Gene transfer to plants*. Springer-Verlag Berlin, 1995)). --

Column 26,
Line 60, "$s^{-1}$" should read -- $S^{-1}$ --.

Column 27,
Line 16, "gus" should read -- GUS --.

Column 28,
Line 28, "Press." should read -- Press, --.

Column 29,
Line 8, "PCAMBIA" should read -- pCAMBIA --.

Column 32,
Line 19, "form" should read -- for --.
Line 66, "m<sup>-</sup>2" should read -- $m^{-2}$ --.

UNITED STATES PATENT AND TRADEMARK OFFICE
CERTIFICATE OF CORRECTION

PATENT NO.    : 6,459,017 B1
DATED         : October 1, 2002
INVENTOR(S)   : Jeknic et al.

It is certified that error appears in the above-identified patent and that said Letters Patent is hereby corrected as shown below:

<u>Column 33,</u>
Lines 13-14, "Nutricot-Type 100[(16N-4.4P-8.3K); Chisso-Asahi®, Fertilizer Co., Ltd., Tokyo, Japan)" should read -- Nutricot-Type 100[(16N-4.4P-8.3K); Chisso-Asahi®, Fertilizer Co., Ltd., Tokyo, Japan] --.
Line 31, "transfer" should read -- transferred --.

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,459,017 B1 Page 1 of 1
APPLICATION NO. : 09/607102
DATED : October 1, 2002
INVENTOR(S) : Jeknic et al.

It is certified that error appears in the above-identified patent and that said Letters Patent is hereby corrected as shown below:

Column 34, line 14, "fluffier" should read --further--.

Signed and Sealed this

Fourteenth Day of October, 2008

JON W. DUDAS
*Director of the United States Patent and Trademark Office*